US011344700B2

(12) United States Patent
Di Caprio et al.

(10) Patent No.: US 11,344,700 B2
(45) Date of Patent: May 31, 2022

(54) BOOSTING CATHETER AND RELATED SYSTEMS AND METHODS

(71) Applicant: QXMedical, LLC, Roseville, MN (US)

(72) Inventors: Fernando Di Caprio, St. Paul, MN (US); Gianfranco Panarello, Mount Royal (CA)

(73) Assignee: QXMedical, LLC, Roseville, MN (US)

( * ) Notice: Subject to any disclaimer, the term of this patent is extended or adjusted under 35 U.S.C. 154(b) by 0 days.

(21) Appl. No.: 16/417,908

(22) Filed: May 21, 2019

(65) Prior Publication Data

US 2019/0275292 A1    Sep. 12, 2019

Related U.S. Application Data

(63) Continuation of application No. 16/188,739, filed on Nov. 13, 2018, now Pat. No. 10,918,830, which is a continuation of application No. 14/864,296, filed on Sep. 24, 2015, now Pat. No. 10,124,146, which is a continuation of application No. 14/210,572, filed on Mar. 14, 2014, now Pat. No. 9,144,662.

(60) Provisional application No. 61/793,982, filed on Mar. 15, 2013.

(51) Int. Cl.
*A61M 25/00* (2006.01)
*A61M 25/01* (2006.01)
*A61M 25/06* (2006.01)

(52) U.S. Cl.
CPC .... *A61M 25/0068* (2013.01); *A61M 25/0069* (2013.01); *A61M 25/0102* (2013.01); *A61M 25/00* (2013.01); *A61M 2025/0004* (2013.01); *A61M 2025/0063* (2013.01); *A61M 2025/0073* (2013.01); *A61M 2025/0175* (2013.01); *A61M 2025/0681* (2013.01)

(58) Field of Classification Search
CPC ........ A61M 25/104; A61M 2025/0004; A61M 25/00; A61M 2025/0175; A61M 2025/0073; A61M 2025/0681; A61M 5/007; A61M 2025/0008; A61M 25/0012; A61M 25/007; A61M 25/0015
See application file for complete search history.

(56) References Cited

U.S. PATENT DOCUMENTS

| | | | |
|---|---|---|---|
| 5,397,321 A * | 3/1995 | Houser | A61B 18/1492 604/528 |
| 5,439,445 A * | 8/1995 | Kontos | A61F 2/88 604/103.1 |
| 5,591,194 A | 1/1997 | Berthiaume | |
| 5,779,671 A | 7/1998 | Ressemann et al. | |
| 5,782,811 A | 7/1998 | Samson et al. | |

(Continued)

FOREIGN PATENT DOCUMENTS

| | | |
|---|---|---|
| EP | 1457230 A1 | 9/2004 |
| JP | H11319074 A | 11/1999 |

(Continued)

*Primary Examiner* — Nilay J Shah
(74) *Attorney, Agent, or Firm* — Sean D. Solberg

(57) ABSTRACT

Disclosed herein is a catheter for positioning through a conventional guiding catheter into the vasculature of a patient, the catheter having a distal tube and a proximal shaft coupled to a proximal portion of the distal tubular member. The distal tube can have a tubular wall, a tube lumen defined within the tube by the tubular wall, a proximal opening sized to allow a medical device to be positioned therethrough, and at least one opening defined within the tubular wall along a length of the distal tube.

15 Claims, 14 Drawing Sheets

(56) References Cited

U.S. PATENT DOCUMENTS

| | | | | |
|---|---|---|---|---|
| 5,830,181 | A * | 11/1998 | Thornton | A61M 25/104 604/102.01 |
| 6,248,100 | B1 | 6/2001 | de Toledo et al. | |
| 2001/0039411 | A1 * | 11/2001 | Johansson | A61B 5/14539 604/509 |
| 2003/0050600 | A1 * | 3/2003 | Ressemann | A61B 17/12109 604/101.01 |
| 2004/0236215 | A1 * | 11/2004 | Mihara | A61M 25/0068 600/434 |
| 2005/0004553 | A1 | 1/2005 | Douk | |
| 2007/0112302 | A1 * | 5/2007 | Yu | A61M 25/0606 604/164.01 |
| 2010/0114062 | A1 | 5/2010 | Wilson et al. | |
| 2010/0217237 | A1 | 8/2010 | Itou et al. | |
| 2011/0021847 | A1 | 1/2011 | Forestiere et al. | |
| 2011/0251519 | A1 | 10/2011 | Romoscanu | |
| 2012/0302953 | A1 * | 11/2012 | Don Michael | A61B 17/22 604/101.05 |
| 2013/0116701 | A1 * | 5/2013 | Wang | A61M 25/01 606/108 |
| 2013/0197483 | A1 | 8/2013 | Anderson et al. | |
| 2013/0237962 | A1 | 9/2013 | Kawai | |

FOREIGN PATENT DOCUMENTS

| | | |
|---|---|---|
| JP | 2007517586 A | 7/2007 |
| JP | 2004275435 A | 10/2007 |
| JP | 2012223207 A | 11/2012 |
| WO | 9403230 | 2/1994 |
| WO | 201119359 A1 | 2/2011 |
| WO | 2011086758 A1 | 7/2011 |
| WO | 2011154128 A1 | 12/2011 |

* cited by examiner

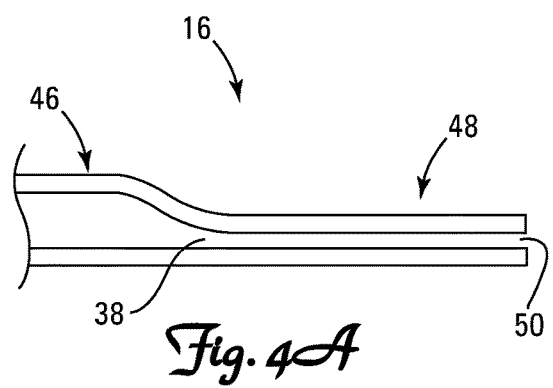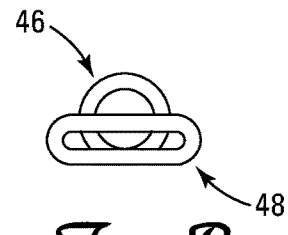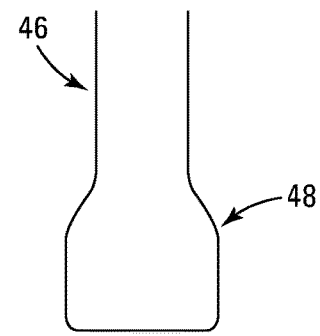
Fig. 4A    Fig. 4B    Fig. 4C
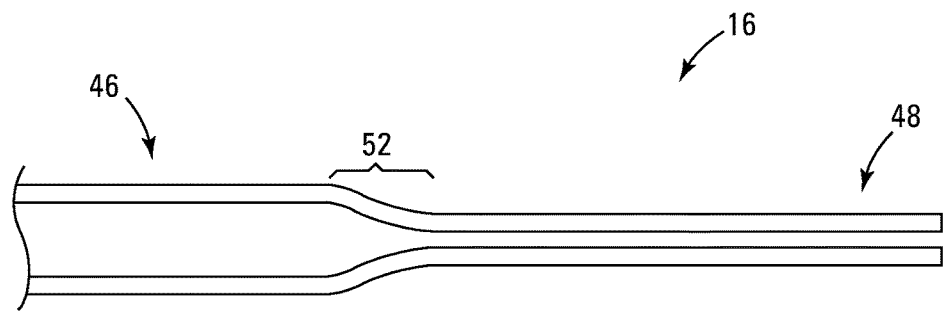
Fig. 5
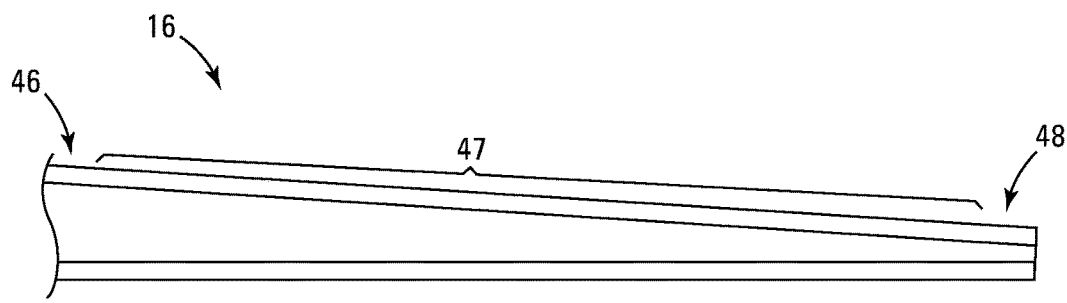
Fig. 6

BOOSTING CATHETER AND RELATED SYSTEMS AND METHODS

CROSS-REFERENCE TO RELATED APPLICATION

This application claims priority as a continuation of U.S. patent application Ser. No. 16/188,739, entitled "Boosting Catheter and Related Systems and Methods," filed on Nov. 13, 2018; which claims priority as a continuation of U.S. Pat. No. 10,124,146, entitled "Boosting Catheter and Related Systems and Methods," which issued on Nov. 13, 2018; which claims priority as a continuation of U.S. Pat. No. 9,144,662, entitled "Boosting Catheter and Related Systems and Methods," which issued on Sep. 29, 2015; which claims priority to U.S. Provisional Application 61/793,982, filed Mar. 15, 2013 and entitled "Extension Guide Catheter," all of which are hereby incorporated herein by reference in their entireties.

FIELD OF THE INVENTION

The various embodiments disclosed herein relate to guiding catheters for use as medical devices, and more particularly to boosting catheters for use with guiding catheter systems.

BACKGROUND OF THE INVENTION

The general use of catheters as medical devices is very well-developed by now. U.S. Pat. No. 4,581,017 to Sahota, for example, shows the use of a guide catheter for insertion into an artery to assist with treating the artery (e.g. with a stenosis); and it further shows the use of another catheter for telescoping insertion into the first catheter to extend beyond the first catheter to treat or access portions of the artery that the first catheter cannot reach because of its larger diameter or lack of flexibility, trackability or support. Subsequent patents show further developments of such telescoping or extension catheter systems. For example, U.S. Pat. No. 5,385,562 to Adams et al., U.S. Pat. No. 5,439,445 to Kontos, and U.S. Pat. No. 5,290,247 to Crittendon all show the use of a catheter having a tubular portion that extends or telescopes beyond the guiding catheter, and an elongated manipulation/insertion wire or shaft attached to the tubular portion to manipulate the tubular portion axially—in push/pull fashion—within the guiding catheter after it has been inserted through the hemostasis valve and into the guiding catheter. The Adams '562 patent suggests that the proximal manipulation/insertion wire may actually be a low-diameter tubular shaft for conducting air to inflate and deflate a restriction balloon that restricts movement of the tubular portion.

According to conventional practice with these types of devices, doctors or technicians often introduce a contrast solution, flushing agent, or therapeutic agent into and through the guiding catheter in order to assist in the viewing of arteries, veins, and other tissues in the body (e.g. by x-ray or flouroscopy) or for other procedural or therapeutic reasons. In some cases, though, it is desirable to limit the use of such solutions because too much of the solution can harm the patient. Introducing the solution through the guiding catheter may result in either too much solution entering the body or the solution not being injected at the correct target location. The diameter of the guiding catheter must be large enough to conduct a variety of tools and devices during the procedure, and so it is not practical to decrease the diameter of the guiding catheter in order to limit the usage of contrast solution.

Accordingly, there has been a need in the art for improved boosting catheters and related methods and system.

SUMMARY OF THE INVENTION

Discussed herein are various boosting catheter embodiments for use with standard guiding catheter.

In Example 1, a boosting catheter comprises a distal tube and a proximal shaft operably coupled to a proximal portion of the distal tube. The distal tube comprises a tubular wall and a tube lumen defined within the tube by the tubular wall. The proximal shaft comprises a shaft lumen defined in the proximal shaft, wherein the proximal shaft is configured to extend distally into a portion of the tube lumen such that the shaft lumen extends distally past a proximal end of the distal tube.

Example 2 relates to the boosting catheter according to Example 1, wherein the proximal shaft further comprises a distal opening in fluidic communication with the shaft lumen, whereby the shaft lumen is in fluidic communication with the tube lumen.

Example 3 relates to the boosting catheter according to Example 2, wherein the shaft lumen is configured to receive fluid such that fluid can be caused to flow distally through the proximal shaft and out of the distal opening.

Example 4 relates to the boosting catheter according to Example 2, wherein the proximal shaft is configured to extend distally into a portion of the tubular wall such that the shaft lumen extends distally into the tubular wall and such that the distal opening is in fluidic communication with the tube lumen.

Example 5 relates to the boosting catheter according Example 2, wherein the proximal shaft is configured to extend distally into a portion of the tubular wall such that the shaft lumen extends distally into the tubular wall and such that the distal opening is in fluidic communication with an area external to the distal tube.

Example 6 relates to the boosting catheter according to Example 1, wherein the proximal shaft comprises at least one elongate member disposed within the shaft lumen.

Example 7 relates to the boosting catheter according to Example 6, wherein the at least one elongate member defines a lumen within the at least one elongate member.

Example 8 relates to the boosting catheter according to Example 6, wherein the at least one elongate member has no lumen.

Example 9 relates to the boosting catheter according to Example 6, wherein the at least one elongate member comprises a first elongate member and a second elongate member, wherein the first elongate member is configured to extend distally into a first portion of the tubular wall, and further wherein the second elongate member is configured to extend distally into a second portion of the tubular wall.

Example 10 relates to the boosting catheter according to Example 9, further comprising a tube disposed in the proximal shaft.

Example 11 relates to the boosting catheter according to Example 1, further comprising at least one support member disposed in the proximal portion of the distal tube.

Example 12 relates to the boosting catheter according to Example 1, wherein a distal portion of the proximal shaft is at least one support member disposed in the proximal portion of the distal tube.

Example 13 relates to the boosting catheter according to Example 1, wherein the shaft lumen is not in fluidic communication with the tube lumen.

Example 14 relates to the boosting catheter according to Example 1, wherein the proximal shaft further comprises a distal opening in fluidic communication with an area external to the distal tube.

In Example 15, a method of using a boosting catheter in combination with a standard guiding catheter to perform a procedure at a predetermined location within the vasculature of a patient comprises positioning the standard guiding catheter into a target vessel in the patient and inserting the boosting catheter into the standard guiding catheter. The method further comprises urging the boosting catheter distally through the standard guiding catheter such that a distal portion of the distal tube extends distally out of the distal end of the standard guiding cathether. In addition, the method comprises performing a procedure through the boosting cathether and standard guiding catheter. Further, the boosting catheter comprises a distal tube and a proximal shaft operably coupled to a proximal portion of the distal tube. The distal tube comprises a tubular wall and a tube lumen defined within the tube by the tubular wall. The proximal shaft comprises a shaft lumen defined in the proximal shaft, wherein the proximal shaft is configured to extend distally into a portion of the tube lumen such that the shaft lumen extends distally past a proximal end of the distal tube.

Example 16 relates to the method according to Example 15, wherein the proximal shaft further comprises a distal opening in fluidic communication with the shaft lumen, whereby the shaft lumen is in fluidic communication with the tube lumen.

Example 17 relates to the method according to Example 16, wherein the performing the procedure further comprises introducing a fluid into the shaft lumen at a proximal end of the proximal shaft, and conducting the fluid distally along the length of the shaft lumen and out of the distal opening.

Example 18 relates to the method according to Example 17, further comprising conducting the fluid distally along the length of the guiding catheter and into the shaft lumen.

Example 19 relates to the method according to Example 15, wherein the performing the procedure further comprises positioning a medical device at the predetermined location through the boosting cathether and guiding catheter, and performing an interventional, diagnostic, or therapeutic procedure using the medical device.

Example 20 relates to the method according to Example 15, wherein the performing the procedure further comprises applying suction at the distal end of the distal tube to remove thrombus, emboli, or debris at the predetermined location by applying a vacuum at a proximal end of the standard guiding catheter.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DESCRIPTION OF DRAWINGS

FIG. 4A is a cross-sectional side view showing the proximal shaft of a boosting catheter, according to one embodiment.

FIG. 4B is an end view showing the proximal shaft of FIG. 4A.

FIG. 4C is a top view showing the proximal shaft of FIG. 4A.

FIG. 5 is a cross-sectional side view of the proximal shaft of a boosting catheter, according to another embodiment.

FIG. 6 is a cross-sectional side view of the proximal shaft of a boosting catheter, according to a further embodiment.

FIG. 19A' is an end view of the proximal shaft of the boosting catheter of FIG. 19A.

FIG. 19D' is a side view of the proximal shaft of the boosting catheter of FIG. 19D, according to one embodiment.

FIG. 19D" is a side view of the proximal shaft of the boosting catheter of FIG. 19D, according to another embodiment.

DETAILED DESCRIPTION

The various embodiments disclosed and contemplated herein relate to a boosting catheter that is adapted to be positioned through and extend distally from a conventional guiding catheter, wherein the guiding catheter is adapted to extend into a patient.

The various boosting catheter embodiments disclosed herein have a distal tubular portion adapted to extend through and beyond the distal end of the guiding catheter. The embodiments also include a proximal elongated shaft connected to the tubular portion at a junction. In certain implementations, the elongated shaft defines a lumen therein (that is, the shaft is hollow or has a hollow-body construction that defines a lumen). The lumen can be configured to conduct fluid along the shaft towards or through the tubular portion or simply to enhance the trackability and passage performance. According to some embodiments, the shaft defines an opening disposed within or in fluid communication with the lumen of the distal tube such that fluid leaving the opening can flow through the tube.

In addition to serving as a conduit for fluids in certain implementations, a manipulation shaft with at least one lumen can have enhanced flexibility both in the axial direction and the longitudinal (or circumferential) direction. This configuration can further enhance the advancement characteristics of the catheter as well as passage of other devices through the guiding catheter (and alongside the manipulation shaft). In addition, the manipulation shaft with the lumen can exhibit a greater propensity to conform to the inner diameter of the guiding catheter, thereby allowing more flexibility and allow enhanced passage of devices within the guiding catheter in the zones occupied by the manipulation shaft.

Figure 1:
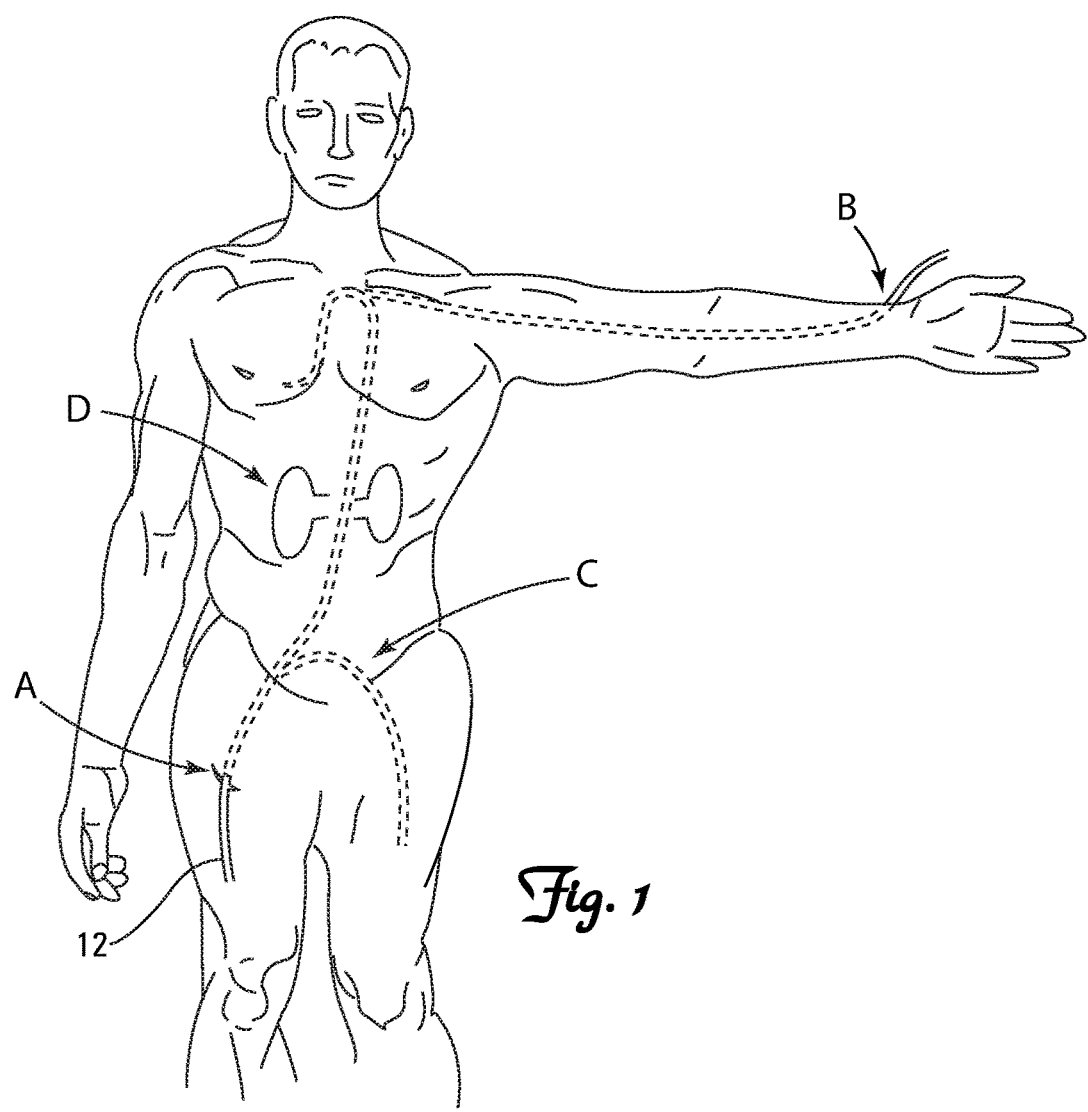
FIG. 1 is an environmental view showing the use of one embodiment of the subject device in a conventional guiding catheter or sheath, which is used to perform various medical procedures.

FIG. 1 depicts a conventional guiding catheter 12 being used in the general operating environment, which is partially within a human body, and usually within an artery or vein. As shown in the figure, the guiding catheter 12 may be inserted into the vasculature through a number of different access points in the body. For example, a femoral artery approach is shown at A, while a radial artery approach is shown at B. Further, other parts of the vasculature may be accessed with various guiding catheters or sheaths. For example, at C, a sheath is shown inserted through the femoral artery for a contralateral approach for procedures in the leg or other parts of the body. In another example, the sheath is inserted through the femoral artery to access the renal arteries in one of the kidneys at D. Regardless of the access point or the target portion of the vasculature, the various boosting cathether implementations disclosed herein can be used in combination with guiding catheters or sheaths to assist with various procedures. For example, the boosting catheter embodiments in combination with guiding catheters or sheaths can be used to assist with the passage of other interventional, diagnostic, or therapeutic devices to various locations in the vasculature. In other instances, the various implementations can be used in combination with guiding catheters or sheaths to assist with the transmission of contrast, diagnostic, or therapeutic fluids/agents by injecting the fluids/agents through the boosting catheter to various locations, or by transmitting the fluids/agents through the guiding catheter via a hemostasis valve and subsequently passing it through the distal tube of the boosting catheter. In another example, the boosting catheter embodiments in combination with guiding catheters or sheaths can be used to assist with the removal of thrombus, emboli, or debris present in the vasculature through the guiding catheter/sheath by applying a vacuum at the proximal end of the guiding catheter/sheath.

Figure 2A:
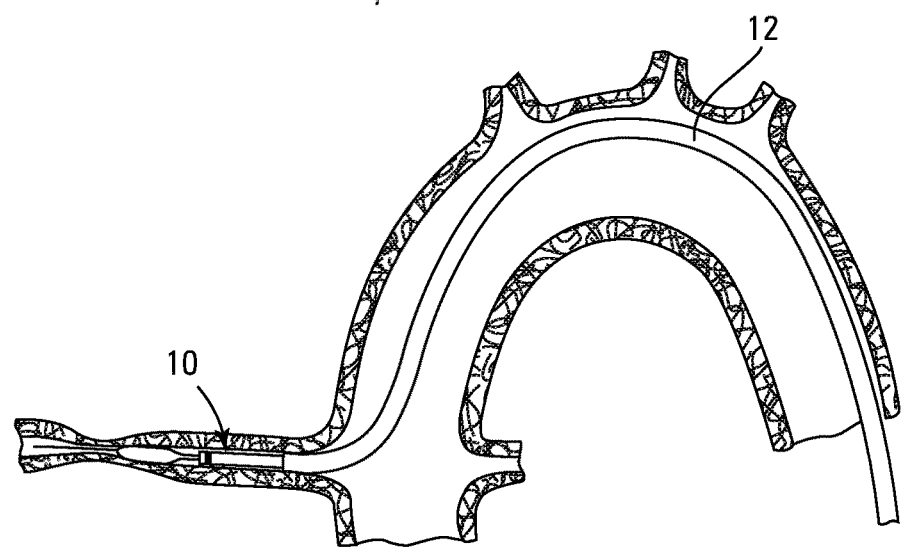
FIG. 2A is a closer environmental view showing the distal end of a boosting catheter extending out the end of a conventional guiding catheter engaged in the coronary vasculature, according to one embodiment.

As shown in FIG. 2A, various embodiments of a boosting catheter (generally shown at 10) as disclosed and contemplated here can be used in conjunction with any conventional guiding catheter 12 for purposes of the various procedures described above. As shown in FIG. 2A, the distal end of the boosting catheter 10 is positioned through and extended distally from the distal end of the conventional guiding catheter 12.

Figure 2B:
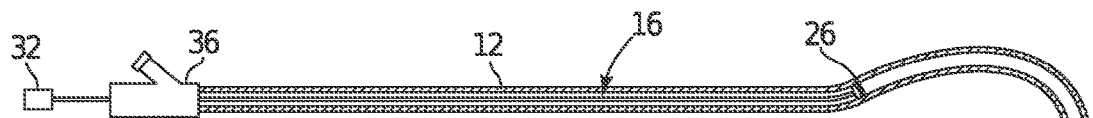
FIG. 2B is another environment view showing a boosting catheter in a guiding catheter and including a proximal portion and a distal portion, according to one embodiment.
Figure 2B:
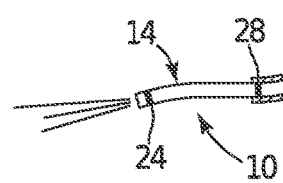
Figure 3A:
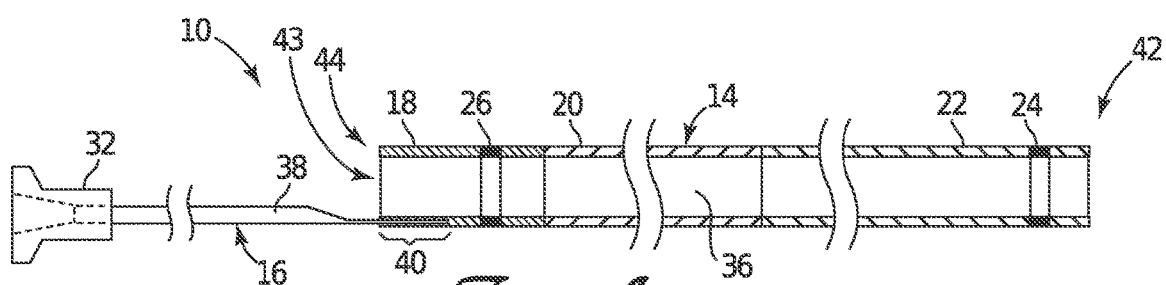
FIG. 3A is a side view in partial section of a boosting catheter with two marker bands, according to one embodiment.
Figure 3B:
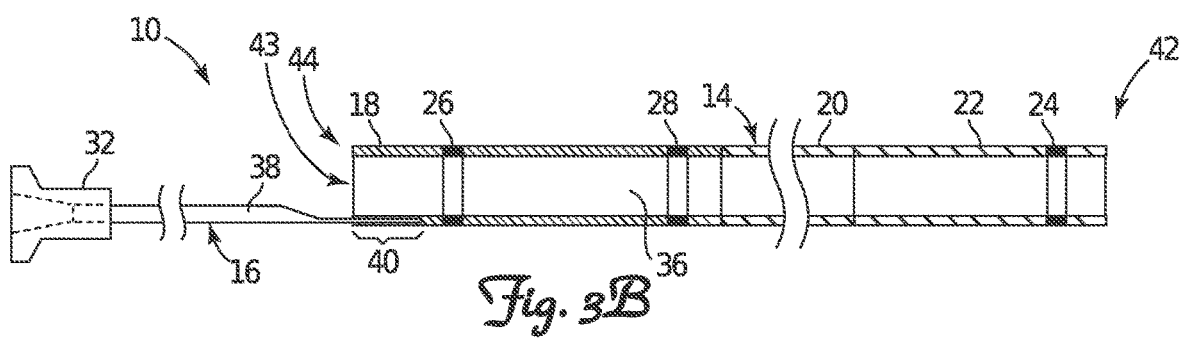
FIG. 3B is a side view in partial section of a boosting catheter with three marker bands, according to another embodiment.
Figure 3C:
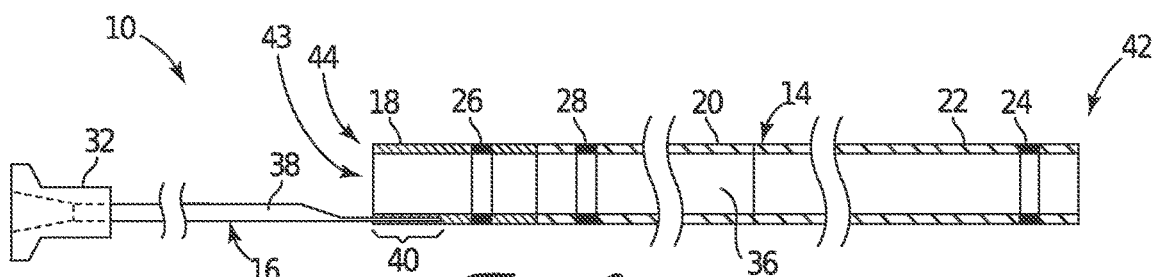
FIG. 3C is a side view in partial section of a boosting catheter with three marker bands, according to a further embodiment.

Certain examples of boosting catheters 10 according to various embodiments are shown in further detail in FIGS. 2B, 3A, 3B, and 3C. Each boosting catheter implementation 10 has two basic parts: a distal portion that is a comparatively large diameter tube (generally indicated at 14) defining a lumen 36; and a proximal portion that is a comparatively smaller diameter elongate member such as a tube or rod, also referred to herein as a "manipulation shaft" (generally indicated at 16). In certain embodiments, as best shown in FIGS. 3A-3C, the manipulation shaft defines at least one lumen 38 along the length of the shaft 16. Alternatively, the proximal portion 16 is a solid wire or rail that is not hollow. The one or more lumens 38 defined within the manipulation shaft 16 can extend to the proximal portion of the tubular shaft 14. The lumen(s) 38 can also extend through or alongside the lumen 36 of the tubular shaft 14 and exit at the very distal end of the shaft 14 or somewhere in between. The lumen 38 may also extend beyond the tubular shaft 14. According to certain embodiments as will be described in further detail below, the one or more lumens 38 are configured to receive a fluid (such as, for example, a contrast solution) such that the fluid can be urged from the proximal end of the lumen 38 to the distal end of the lumen 38 and thereby dispense or deliver the fluid out of the distal end of the shaft 16.

The larger diameter tube 14 is, according to one embodiment, made generally from flexible polymeric materials. The tube 14 can have, in one specific example, a PEBAX, polyurethane, or NYLON outer layer, and a PTFE inner layer. The tube 14 may also incorporate re-enforcing coil or mesh. The tube 14 may also incorporate radiopaque markers (such as markers 24, 26, or 28 as discussed below) on the tube 14. The manipulation shaft 16 may also incorporate one or more visual markers, including radiopaque markers.

As shown in FIGS. 3A, 3B, and 3C, certain embodiments of the larger diameter tube 14 can have three segments or more of differing flexibilities: a low flexibility segment 18 at the proximal end of the tube 14, a medium flexibility segment 20 in the middle 20 of the tube 14, and a high flexibility segment 22 at the distal end. More segments of varying flexibilities can also be used. In fact, the transition zone 40 (the area of overlap in which the manipulation shaft 16 is coupled to the larger tube 14) has varying flexibility in that zone 40. The differing flexibilities can be accomplished through combinations of differing materials, configurations, or geometries as is known in the art (e.g. mesh or coil reinforcing, different PEBAX varieties, etc.). Moreover, different lengths can be selected for the segments 18, 20, 22 and the transition zone 40 according to design considerations. For example, if the smaller diameter shaft 16 has at least one lumen 38, then the low flexibility segment 18 may be longer to obtain optimal advancement characteristics. This permits more flexibility along a greater length of the boosting catheter 10 as needed to deal with anticipated curvature in the path the catheter 10 must follow. An example of this is illustrated in FIG. 2B, which shows the smaller diameter tube 16 terminating where anticipated curves begin.

As mentioned above, the flexible tube 14 can have radiopaque markers embedded in the tube 14 and placed along the length of the tube 14 for various purposes. For example, marker 24 can be used at or near the distal tip 42 of the tube 14 to help the doctor locate the position of the tip 42. Another marker 26 could be used at or near the proximal end 44 of the tube 14 to assist the doctor in locating that end 44 of the tube 14 relative to the end of the guiding catheter or to assist in visualizing the location of the proximal opening of the tube 14. In one embodiment, the marker band 26 can be located near the proximal end 44 of the tube but at a position on the tube 14 that is distal to the end 44, as shown in FIGS. 3A-3C.

Further, in certain embodiments, a radiopaque marker (not shown) can be located anywhere in or near the transition zone 40 (e.g. on the manipulation shaft 16 in or near the transition zone 40 or in the distal tube 14 in the transition zone 40). Further, any of the markers 24, 26, 28 can be non-cylindrical. For example, one or more of the markers 24, 26, 28 can be strips or other known configurations.

One or more of these markers 24, 26, 28 can be helpful to indicate to the doctor or surgeon the location of the proximal end 44 of the tube 14 in relation to the guiding catheter (such as catheter 12) so that they do not insert or push the proximal end 44 past the distal end of the guiding catheter 12. In this regard, certain embodiments include a third marker 28 located at some optimal point along the tube 14 in between the other two markers 24 and 26, as shown in FIGS. 2B, 3B, and 3C. As shown best in FIG. 2B, the doctor or surgeon can use this third marker 28 to track how far the tube 14 is extending beyond the guiding catheter 12. That is, the third marker 28 can be used in certain circumstances as a limit indicator. For example, in a specific embodiment having a tube 14 that is 35 cm in length, the third marker band 28 may be located 15 cm from the distal end 42 of the tube 14 in order to indicate this predetermined distance to the doctor, such that the doctor knows the distance that the distal end 42 extends beyond the guide catheter 12. Depending on the specific configuration of the boosting catheter 10, the third marker band 28 can be disposed in the low flexibility segment 18, the middle flexibility segment 20, or possibly even in the high flexibility segment 22.

It is understood that the distal tube 14 can have one, two, three, or more markers as described above. It is further understood that any marker arrangement of one or more markers, including the three marker arrangement, can be used in connection with a variety of boosting catheter configurations, including those having a solid rail (e.g. a flat or round wire) or a hollow rail or proximal section with a lumen, such as a tube. In other implementations, one or more markers can be positioned on the shaft 16.

In one implementation, the proximal portion 16 is an elongate member 16 (such as a tube) having a lumen defined therein, wherein the elongate member 16 is made of at least one metal and/or at least one polymer. One example of a metal that can be used is stainless steel, such as 304 or 316 grade stainless steel. According to certain embodiments, the tube 16 can be coated (for additional lubricity, for example) with one or more materials such as TEFLON or PTFE, or with another hydrophilic coating, or a hydrophobic coating (like silicone). The tube can also be made from nitinol (nickel-titanium) for improved kink resistance.

In certain embodiments, the manipulation shaft 16 is coupled to the distal tube 14 such that the shaft 16 and the lumen 38 defined in the shaft 16 extend into or through the distal tube 14. Various shaft 16 configurations can be used for this purpose. For example, FIGS. 4A-4C depict a distal portion of a manipulation shaft 16 having a full diameter section 46 and a reduced diameter section 48 at the distal end of the shaft 16. FIG. 4A depicts a side view of the shaft 16, while FIG. 4B shows a front view of shaft 16 and FIG. 4C provides a top view of the shaft 16. As best shown in FIGS. 4B and 4C, the reduced diameter section 48 has a substantially ovular cross-section, while the full diameter section 46 has a substantially circular cross-section. As best shown in FIG. 4A, the lumen 38 of the shaft 16 extends through both the full diameter 46 and reduced diameter 48 sections.

Certain embodiments, including the embodiment shown at FIGS. 4A-4C, are configured to be capable of dispersing fluids through the shaft 16, including fluids such as contrast solution, saline solution, or therapeutic solutions. For example, the shaft 16 in FIGS. 4A-4C has a lumen 38 and a distal opening 50 configured to allow for fluids to pass through the lumen 38 and be dispersed out of the opening 50. Further, the reduced diameter section 48 with the lumen 38 is configured to be coupled to the distal tube 14 such that a distal portion of the reduced diameter section 48 is integrated into a proximal portion of the tube 14 in the transition zone (such as transition zone 40) as discussed in further detail below. Alternatively, the reduced diameter section 48 with the lumen 38 need not be used to transfer or disperse fluids and instead can simply be configured to be coupled to the distal tube 14 as disclosed herein. In such embodiments as will be described in further detail below, the lumen 38 is configured to have a distal opening (such as distal opening 50 discussed above) that places the lumen 38 in fluid communication with either the lumen 36 of the distal tube 14 or an exterior area of the distal tube 14. Alternatively, the manipulation shaft 16 can be configured to have no distal opening and thus have a lumen that is not in fluid communication with the distal tube 14 or anything else at its distal end.

There can be benefits of a proximal portion having a lumen. As discussed above, it allows for transmission of fluid through a conduit that is smaller in diameter than the guiding catheter. In certain embodiments, the lumen is sized specifically to conduct the desired amount of a specific fluid into the distal tube, into a wall of the distal tube, out of the wall of the distal tube through an opening somewhere along the length of the tube, or out of the distal end of the distal tube. The control of the lumen size can allow for transmission of more or less fluid, depending on what is desired. For example, less fluid can be desirable when the fluid is contrast solution that is typically used in several catheter-based procedures, because greater amounts of contrast solution can cause harm to the patient.

Additional configurations of the distal end of the manipulation shaft 16 are shown in FIGS. 5 and 6. In the embodiment shown in FIG. 5, the transition section 52 between the full diameter section 46 and the reduced diameter section 48 involves a narrowing around the full circumference of the shaft 16 as shown (in contrast to a narrowing of one portion of the shaft 16 as shown in FIG. 4A). Alternatively, FIG. 6 depicts a shaft 16 having an extended tapered section 47 from the full diameter section 46 to the reduced diameter section 48.

The various manipulation shaft 16 embodiments as discussed in further detail elsewhere herein provide for a gradual change in flexibility from the proximal end of the shaft 16 to the distal end. Further, certain shaft implementations are configured such that the distal portion of the shaft 16 couples with the tube 14 in such a way as to maximize the inner diameter (the lumen 36) of the tube 14. That is, in certain implementations, the various boosting catheters 10 disclosed or contemplated herein require a sufficiently accessible opening 43 (as best shown in FIGS. 3A-3C) at the proximal end 44 of the distal tube 14 to allow for the lumen 36 to be accessible for medical devices. In other words, the opening 43 must be large enough and/or have sufficient clearance to allow for easy insertion of various medical devices into the opening 43 such that the devices can be urged distally through the tube 14 and out of the opening at the distal end 42 of the tube 14. In certain of these embodiments, clearance at the opening 43 at the proximal end 44 of the distal tube 14 can be optimized by minimizing the profile (by reducing the diameter, etc.) of the manipulation shaft 16 according to various configurations as disclosed herein.

As mentioned above, in accordance with some embodiments, the distal portion of the manipulation shaft 16 is integrated or embedded in the proximal end of the distal tube 14. For example, in certain implementations, the distal tube 14 is molded over the distal end of the manipulation shaft 16, thereby creating a transition zone such as the zone 40 discussed above.

Figure 7A:
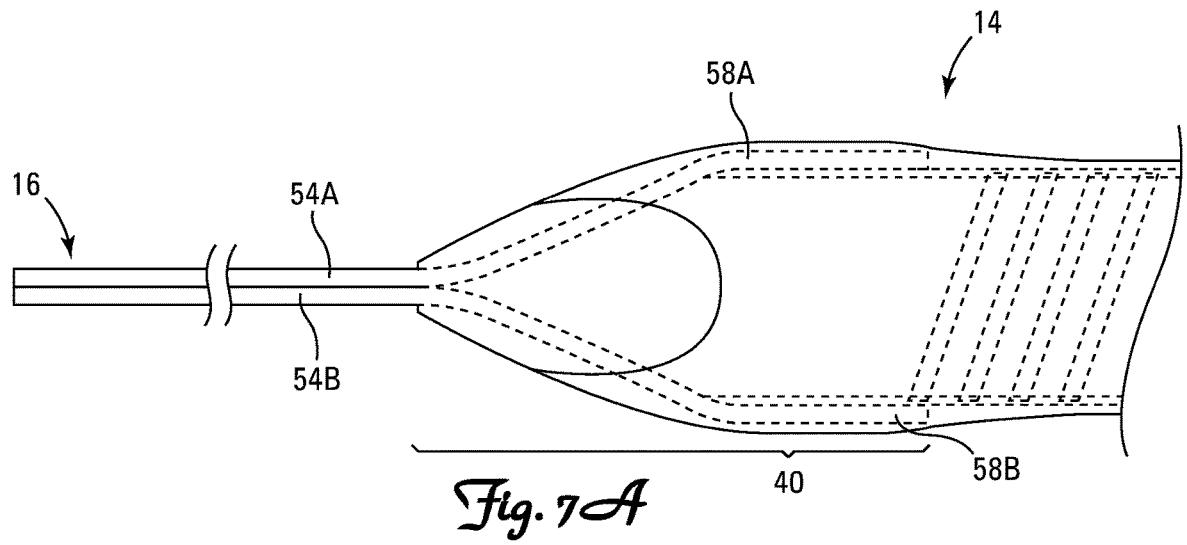
FIG. 7A is a top view of a boosting catheter showing the junction of the proximal and distal portions, according to one embodiment.
Figure 7B:
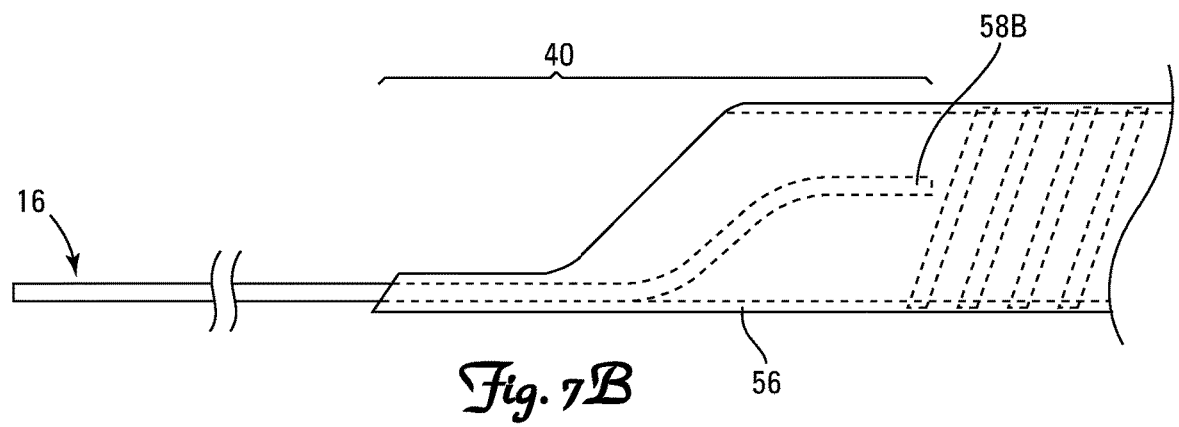
FIG. 7B is a cross-sectional side view of the boosting catheter of FIG. 7A.
Figure 7C:
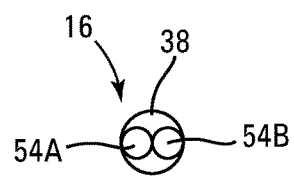
FIG. 7C is a cross-sectional end view of the proximal shaft of the boosting catheter of FIG. 7A.
Figure 8A:
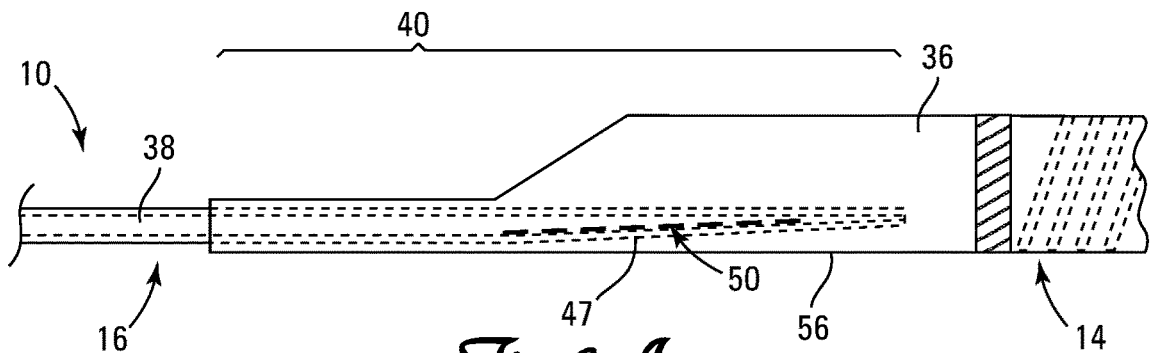
FIG. 8A is a cross-sectional side view of a boosting catheter showing the junction of the proximal and distal portions, according to one embodiment.
Figure 8B:
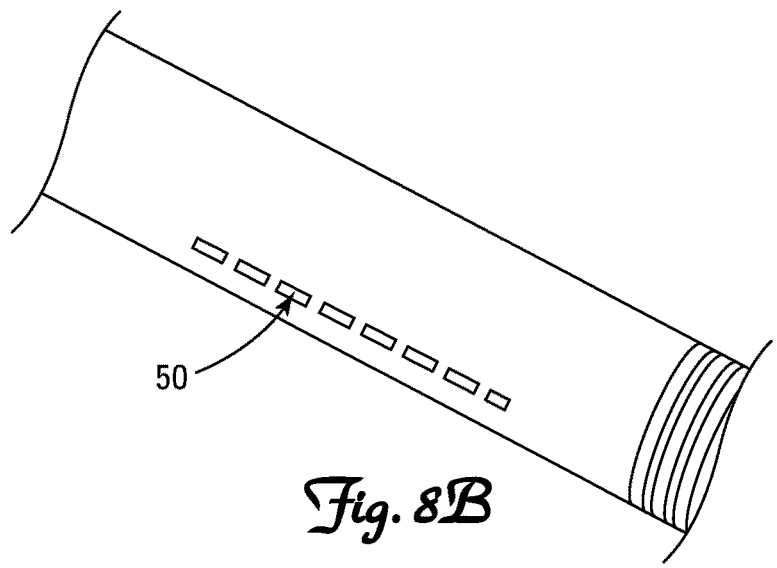
FIG. 8B is a is a perspective view of a portion of the junction of the proximal and distal portions of the boosting catheter of FIG. 8A.

In certain embodiments, the distal end of the manipulation shaft 16 may be coupled to the distal tube 14 in an eccentric manner, rather than a concentric manner. That is, the shaft 16 is joined to the distal tube 14 at one point or in one zone of the periphery or circumference of the distal tube 14 ("eccentrically"), rather than being joined together around the entire circumference of the shaft 16 and tube 14. For example, in one implementation as shown in FIGS. 7A-7C, the manipulation shaft 16 is coupled to the distal tube 14 at a point or area of the wall 56 of the tube 14. The shaft 16 in this embodiment is made up of two rods 54A, 54B positioned within the lumen 38 of the shaft 16, as best shown in FIG. 7C. In one embodiment, the rods 54A, 54B are solid (that is, they do not have lumens). Alternatively, the rods 54A, 54B can be hypotubes 54A, 54B, with each having a lumen defined therein. As best shown in FIGS. 7A and 7B, a distal portion of the shaft 16 is coupled to and integral with an outer wall 56 of the distal tube 14 at the transition zone 40. Further, as best shown in FIG. 7A, the two rods 54A, 54B extend from the distal portion of the shaft 16 such that the distal portions 58A, 58B of the rods 54A, 54B extend into the distal tube 14. More specifically, the distal portion 58A of rod 54A is disposed in the wall 56 of the distal tube 14 at a position that is on the opposite side of the wall 56 across the lumen 36 from the distal portion 58B. Further, as best shown in FIG. 7B, both distal portions 58A, 58B (only 58B is visible in FIG. 7B because of the location of distal portion 58A behind distal portion 58B in the figure) extend at an angle toward a vertical midpoint of the tube 14 and extend horizontally along that position for some distance as well as shown. In accordance with one implementation, the positioning of the distal portions 58A, 58B of the rods 54A, 54B in the wall 56 of the distal tube 14 enhances the kink resistance of that portion of the tube 14 as well as assisting in transmitting a distal or proximal force to the distal tube 14 in a more even fashion during use of the catheter 10.

Additional embodiments of manipulation shafts 16 coupled to distal tubes 14 are shown in FIGS. 8A-10. The device 10 depicted in FIGS. 8A and 8B has a manipulation shaft 16 coupled to the distal tube 14 such that a distal portion of the manipulation shaft 16 is positioned within the lumen 36 of the tube 14 or integrated into an outer wall 56 in the transition zone 40 of the tube 14. In this embodiment, the tapered portion 47 of the shaft 16 is a taper along one side of the shaft 16 such that the tapered portion 47 is an angled portion 47 on the side of the shaft 16 opposite the lumen 36 of tube 14. Hence, the opening 50 at the distal end of the shaft 16 is along the tapered portion 47 of the distal end of the shaft 16 such that the opening 50 faces away from the lumen 36 of the tube 14. In this specific embodiment as best shown in FIG. 8B, the opening 50 is actually made up of multiple openings 50 defined along the tapered portion 47 of the shaft 16 and outer wall 56 of the distal tube in fluid communication with the lumen 38. Alternatively, the opening 50 can be a single opening, two openings, or any number of openings. In this exemplary implementation, the lumen 38—via the openings 50 in the shaft 16 and wall 56—is in fluid communication with an area or space outside the distal tube 14. Alternatively, the openings 50 can be on the side of the shaft 16 facing the lumen 36 of tube 14 such that the lumen 38 is in fluid communication with the lumen 36 of tube 14. In a further embodiment, the shaft 16 has no opening at the distal end of the shaft 16 and thus, while the distal end of the shaft 16 is positioned within the distal tube 14 or some portion thereof, the lumen 38 is not in fluid communication with the distal tube 14 or any portion thereof.

Figure 9:
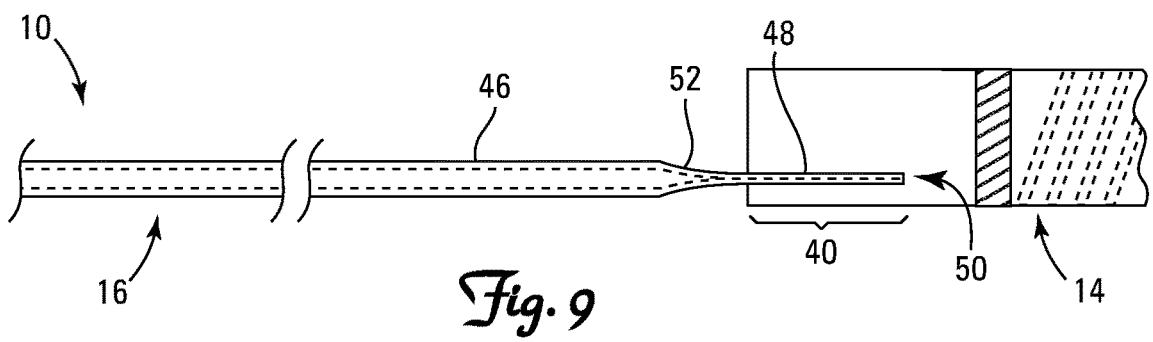
FIG. 9 is a cross-sectional side view of a boosting catheter showing the junction of the proximal and distal portions, according to another embodiment.

The device 10 shown in FIG. 9 has a manipulation shaft 16 coupled to the distal tube 14 such that a distal portion of the manipulation shaft 16 is positioned within the lumen 36 of the tube 14 or integrated into an outer wall 56 in the transition zone 40 of the tube 14. In this embodiment, the transition section 52 from the full diameter section 46 to the reduced diameter section 48 of the shaft 16 is a taper around the entire circumference of the shaft 16 as shown. In this embodiment, the transition section 52 is positioned outside the lumen 36 (or the outer wall 56) of the distal tube 14, and the opening 50 at the distal end of the shaft is positioned within the lumen 36. In this exemplary implementation, the opening 50 is in direct fluid communication with the lumen 36 of tube 14 or is integrated into the outer wall 56 and is in fluid communication with the lumen 36 via an opening in the wall 56 of the tube 14.

Figure 10:
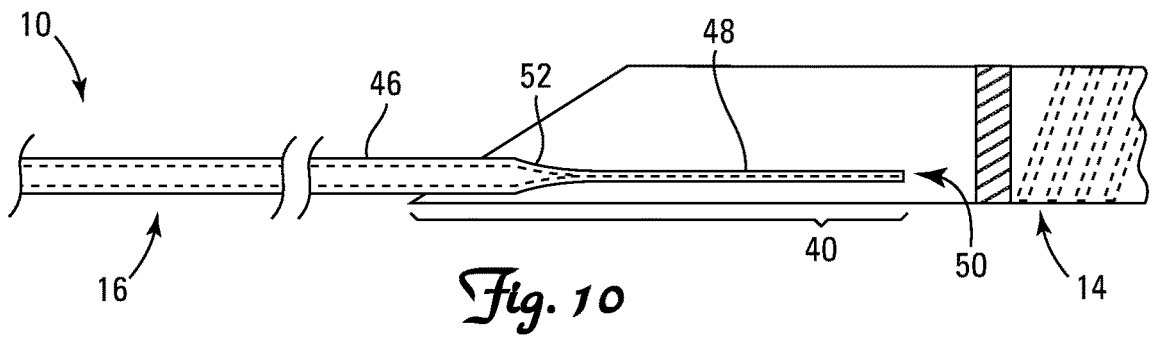
FIG. 10 is a cross-sectional side view of a boosting catheter showing the junction of the proximal and distal portions, according to a further embodiment.

The device 10 shown in FIG. 10 has a manipulation shaft 16 coupled to the distal tube 14 such that a distal portion of the manipulation shaft 16 is positioned within the lumen 36 of the tube 14 or integrated into an outer wall 56 in the transition zone 40 of the tube 14. In this embodiment, the transition section 52 of the shaft 16 is a taper 52 around the entire circumference of the shaft 16 as shown. In this embodiment, the transition section 52 is positioned within the lumen 36 (or the outer wall 56) of the distal tube 14 such that the entire reduced diameter section 48 is positioned within the lumen 36 (or the outer wall 56). In this exemplary implementation, the opening 50 is in direct fluid communication with the lumen 36 of tube 14 or is integrated into the outer wall 56 and is in fluid communication with the lumen 36 via an opening in the wall 56 of the tube 14. Alternatively, the lumen 38 of the shaft 16 is not in fluid communication with the lumen 36 of tube 14.

It is understood that the manipulation shaft 16 in these embodiments of FIGS. 8-10 can have a single lumen 38. Alternatively, the shaft 16 of any of the three embodiments can have a lumen 38 containing one or two elongate members in a fashion similar to the shaft 16 described above with respect to FIGS. 7A-7C. In another alternative, the shaft 16 can be configured in any fashion as described elsewhere herein.

Figure 11:
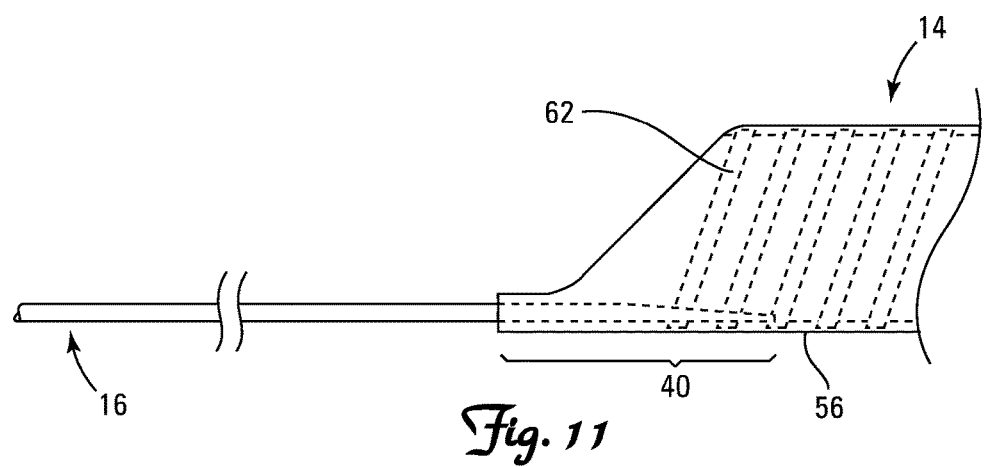
FIG. 11 is a cross-sectional side view of a boosting catheter showing the junction of the proximal and distal portions, according to yet another embodiment.

The device 10 shown in FIG. 11 has a manipulation shaft 16 coupled to the distal tube 14 such that a distal portion of the manipulation shaft 16 is positioned within the lumen 36 of the tube 14 or integrated into an outer wall 56 in the transition zone 40 of the tube 14. In this embodiment, the reinforcing coil 62 of the tube 14 extends proximally into the transition zone 40 and has a larger pitch in the transition zone 40. That is, the separate strands of the coil 62 are farther apart in the transition zone 40. According to one embodiment, this larger pitch results in lesser reinforcement or support by the coil 62 in that area of the tube 14. In certain embodiments, this is because the distal portion of the shaft 16 in the transition zone 40 provides additional support or reinforcement.

Figure 12:
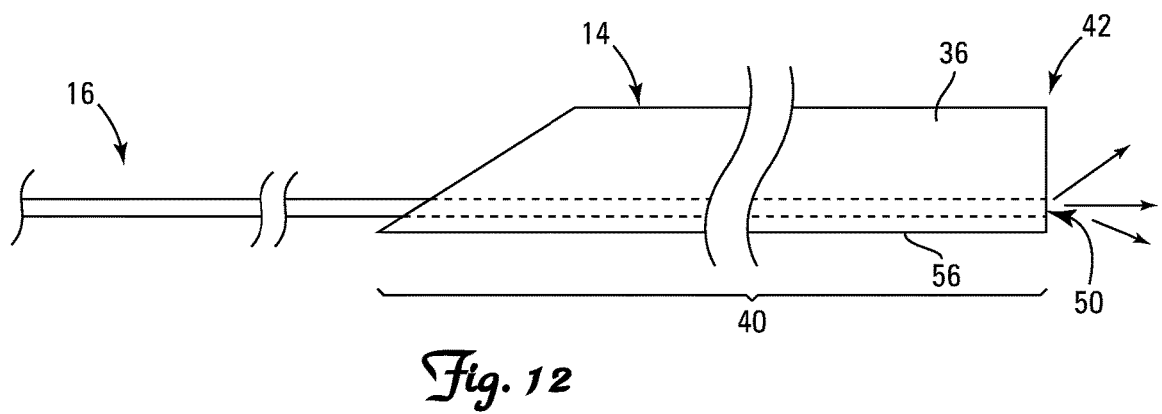
FIG. 12 is a cross-sectional side view of a boosting catheter showing the junction of the proximal and distal portions, according to another implementation.

The device 10 shown in FIG. 12 has a manipulation shaft 16 coupled to the distal tube 14 such that a distal portion of the manipulation shaft 16 is positioned within the lumen 36 of the tube 14 or integrated into an outer wall 56 in the transition zone 40 of the tube 14. In this embodiment, the distal portion of the shaft 16 has no tapered portion and extends along the entire length of the distal tube 14 such that the opening 50 of the shaft 16 is positioned at the opening in the distal end 42 of the tube 14. Alternatively, the shaft 16 can extend distally out of the opening at the distal end 42 of the tube 14.

Figure 13:
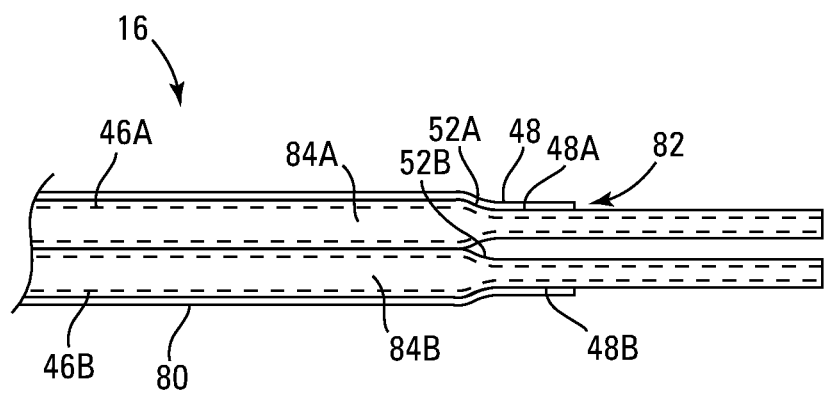
FIG. 13 is a cross-sectional top view of a proximal shaft of a boosting catheter, according to one embodiment.

As discussed above, certain implementations of the proximal shaft 16 have a tube defining a lumen in which two separate inner elongate members are positioned. For example, the manipulation shaft 16 shown in FIG. 13 has an outer tube 80 defining a lumen 82 with two inner elongate members 84A, 84B positioned therein. The shaft 16 has a reduced diameter portion 48 in which both of the elongate members 84A, 84B have reduced diameter portions 86A, 86B as shown. In this exemplary embodiment, each elongate member 84A, 84B has a transition section 52A, 52B between the full diameter section 46A, 46B and the reduced diameter section 48A, 48B that involves a narrowing around the full circumference of the members 84A, 84B as shown.

Figure 14:
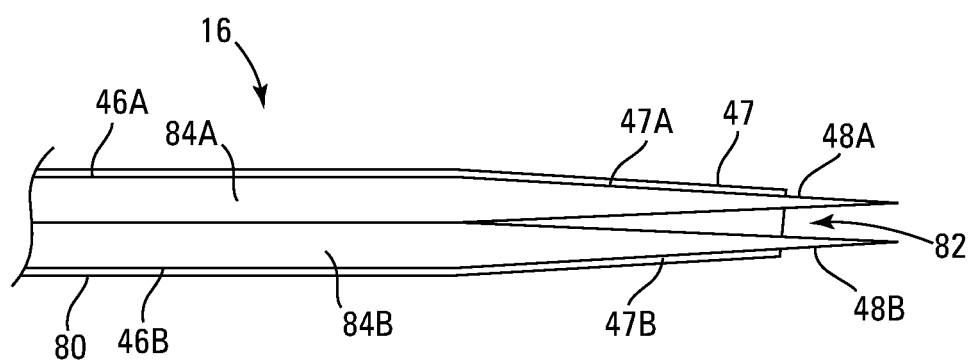
FIG. 14 is a cross-sectional top view of a proximal shaft of a boosting catheter, according to another embodiment.

Alternatively, the manipulation shaft 16 shown in FIG. 14 has an outer tube 80 defining a lumen 82 with two inner elongate members 84A, 84B positioned therein. The shaft 16 has a tapered section 47 in which both of the elongate members 84A, 84B have tapered sections 47A, 47B as shown. In this exemplary embodiment, each elongate member 84A, 84B has an extended taper from the full diameter section 46A, 46B to the reduced diameter section 48A, 48B.

Figure 15A:
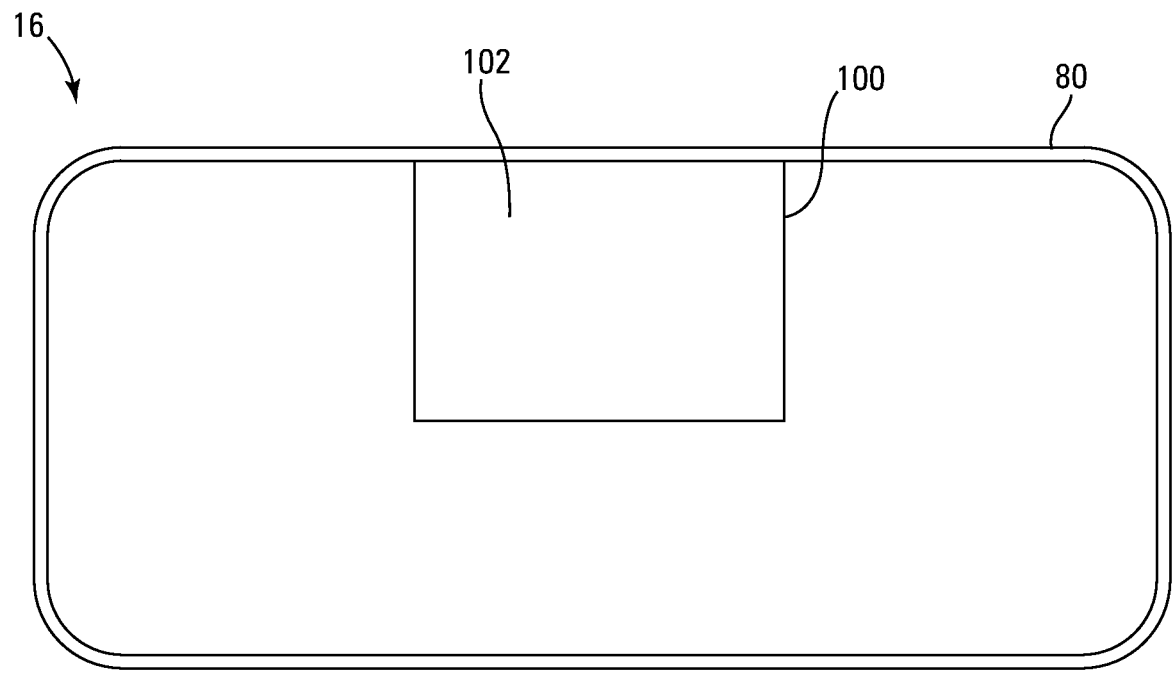
FIG. 15A is a cross-sectional view of a proximal shaft of a boosting catheter, according to a further embodiment.
Figure 15B:
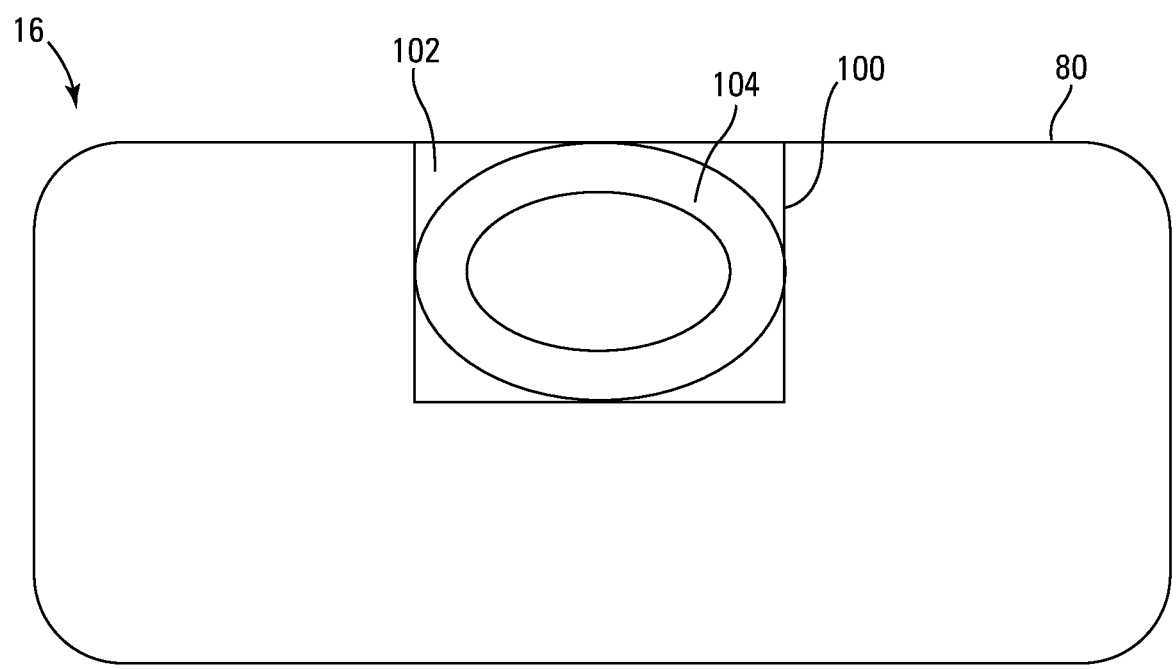
FIG. 15B is a cross-sectional view of another proximal shaft of a boosting catheter, according to yet another embodiment.

As mentioned above with respect to certain specific embodiments, the cross-sectional configuration of the manipulation shaft 16 can take any number of different forms. For example, FIGS. 15A and 15B depict cross-sectional configurations of different manipulation shaft 16 embodiments. FIG. 15A depicts a shaft 16 comprised of an elongate member 16 having a metal body 100 with a square or parallelogram-shaped cross-section and a polymeric outer coating 80. The metal body 100 defines a lumen 102 in the body 100 that runs along the entire length of the body 100.

In an alternative configuration as shown in FIG. 15B, the shaft 16 has an elongate member 16 with a metal body 100 having a square or parallelogram-shaped cross-section and a polymeric outer coating 80. In addition, the metal body 100 defines a lumen 102 in the body 100 that runs along the entire length of the body 100. Further, a tube 104 is provided that is positioned within the lumen 102 in the body 100. The tube 104 can be made of metal or a polymeric material. In a further embodiment, the tube 104 is a polymeric coating 104 that is configured to line the lumen 102.

Figure 16A:
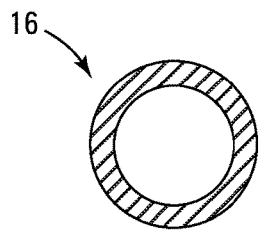
FIG. 16A is a cross-sectional view of a proximal shaft of a boosting catheter, according to one implementation.
Figure 16B:
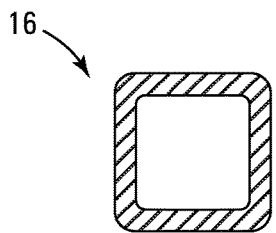
FIG. 16B is a cross-sectional view of a proximal shaft of a boosting catheter, according to another implementation.
Figure 16C:
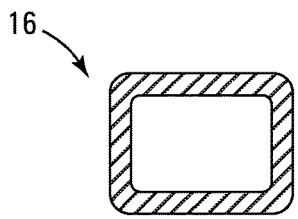
FIG. 16C is a cross-sectional view of a proximal shaft of a boosting catheter, according to a further implementation.
Figure 16D:
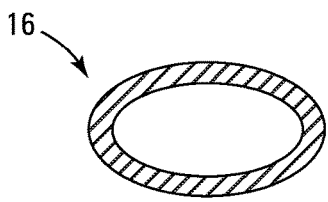
FIG. 16D is a cross-sectional view of a proximal shaft of a boosting catheter, according to yet another implementation.
Figure 16E:
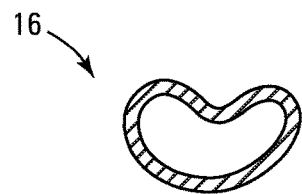
FIG. 16E is a cross-sectional view of a proximal shaft of a boosting catheter, according to another embodiment.
Figure 16F:
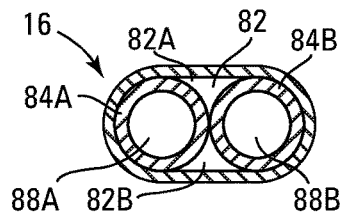
FIG. 16F is a cross-sectional view of a proximal shaft of a boosting catheter, according to a further embodiment.
Figure 16G:
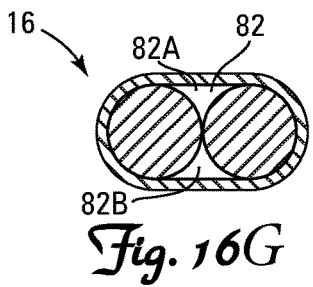
FIG. 16G is a cross-sectional view of a proximal shaft of a boosting catheter, according to yet another embodiment.
Figure 16H:
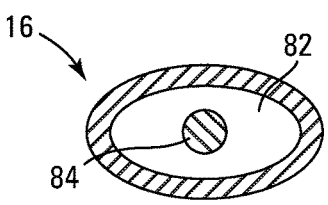
FIG. 16H is a cross-sectional view of a proximal shaft of a boosting catheter, according to another implementation.
Figure 16I:
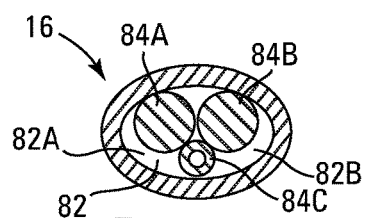
FIG. 16I is a cross-sectional view of a proximal shaft of a boosting catheter, according to a further implementation.

FIG. 16A depicts the cross-section of the manipulation shaft 16 according to another embodiment in which the shaft 16 is a hollow tube 16 with a circular cross-section. FIG. 16B depicts a shaft 16 that is a hollow tube 16 with a relatively square cross-section. FIG. 16C shows a shaft 16 that is a hollow tube 16 with a relatively rectangular cross-section. FIG. 16D depicts a shaft 16 that is a hollow tube with a relatively ovular cross-section. FIG. 16E shows a shaft 16 that is a hollow tube 16 with a relatively kidney bean-shaped cross-section. The shaft 16 in FIG. 16F is an elongate member 16 with a lumen 82 in which two smaller, hollow elongate members 84A, 84B are disposed. FIG. 16G depicts an elongate member 16 with a lumen 82 in which two smaller, solid (non-hollow) elongate members 84A, 84B are disposed. FIG. 16H shows an elongate member 16 having a substantially ovular cross-section with a lumen 82 in which a single smaller elongate member 84 is disposed. FIG. 16I depicts an elongate member 16 with a lumen 82 in which two smaller, solid (non-hollow) elongate members 84A, 84B and a third smaller hollow elongate member 84C are disposed.

With respect to the shafts 16 shown in FIGS. 16F, 16G, 16H, and 16I, the additional smaller elongate members 84A, 84B, 84C disposed within the lumen 82 of the shaft 16 add support or reinforcement to the shaft 16 while also having multiple lumens within the shaft 16. For example, the shaft 16 in FIG. 16F has two lumens 88A, 88B in the two elongate members 84A, 84B, along with two lumens 82A, 82B created in the spaces on either side of the two elongate members 84A, 84B. Similarly, it should be noted that the shaft 16 configurations described above and depicted in FIGS. 7A-7C, 13, and 14 have similar configurations that also have lumens in the spaces created by the elongate members disposed therein. The shaft 16 in FIG. 16G has two lumens 82A, 82B created in the spaces on either side of the two solid (non-hollow) elongate members 84A, 84B. In FIG. 16H, the shaft 16 has a single larger lumen 82 defined by the shaft 16 with the single elongate member 84 disposed therein. In FIG. 16I, the shaft 16 has a lumen 88 within the hollow elongate member 84C and two lumens 82A, 82B in the spaces on either side of the member 84C. Further, it is understood that any of these configurations as shown in FIGS. 16A-16I can be any combination or number of solid and/or hollow elongate members.

In some embodiments, the elongate members 84A, 84B, 84C are slideably disposed within the shaft 16, such that the elongate members 84A, 84B, 84C are slideable in relation to the shaft 16 and each other. Alternatively, the elongate members 84A, 84B, 84C are joined, bonded, or otherwise coupled to each other such that they are not slidable in relation to each other. In a further implementation, the elongate members 84A, 84B, 84C can be coupled or otherwise joined to each other and to the shaft 16 such that they are not slideable in relation to each other or the shaft 16.

According to various embodiments, the manipulation shaft 16 can have a diameter that ranges from about 0.01 inches to about 0.03 inches (or can have a size that ranges from about ¼ French to about 3 French). The various inner elongate members can be made of stainless steel, nitinol, or other similar metals. In those embodiments with inner elongate members, the outer wall of the shaft 16 is made of polymeric materials such as PET, PTFE, Teflon, FEP, PE, PEBA, or other similar materials.

Figure 17A:
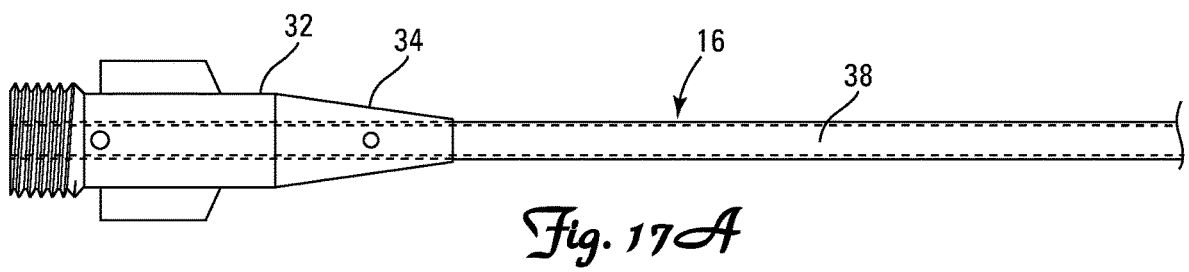
FIG. 17A is a cross-sectional side view of a proximal shaft of a boosting catheter, according to one embodiment.

As shown in FIGS. 2B and 17A, the manipulation shaft 16 can terminate in a proximal fitting 32. In accordance with one embodiment, the fitting 32 is adapted for connection to a fluid source. In certain embodiments, the fitting 32 is a standard female luer connection that is made from plastic. The fitting 32 can be bonded to the manipulation shaft 16 with adhesive, or it can be insert-molded over the manipulation shaft 16. In the embodiment shown in FIG. 17A, there is an optional strain-relief segment 34 disposed between the manipulation shaft 16 and the proximal fitting 32. The strain relief segment 34 provides a flexible transition from the manipulation shaft 16 to the proximal fitting 32.

Figure 17B:
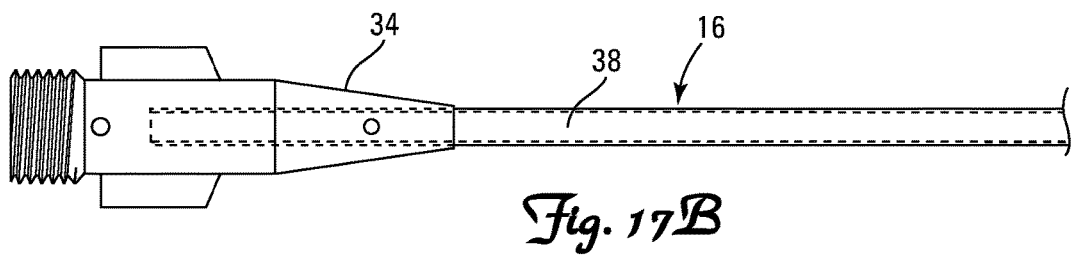
FIG. 17B is a cross-sectional side view of a proximal shaft of another boosting catheter, according to a further embodiment.

Alternatively, in FIG. 17B, the proximal end of the lumen 38 in the shaft 16 does not have an opening. That is, the proximal end of the lumen 38 is not in fluid communication with any opening at the proximal end of the shaft 16.

Figure 18A:
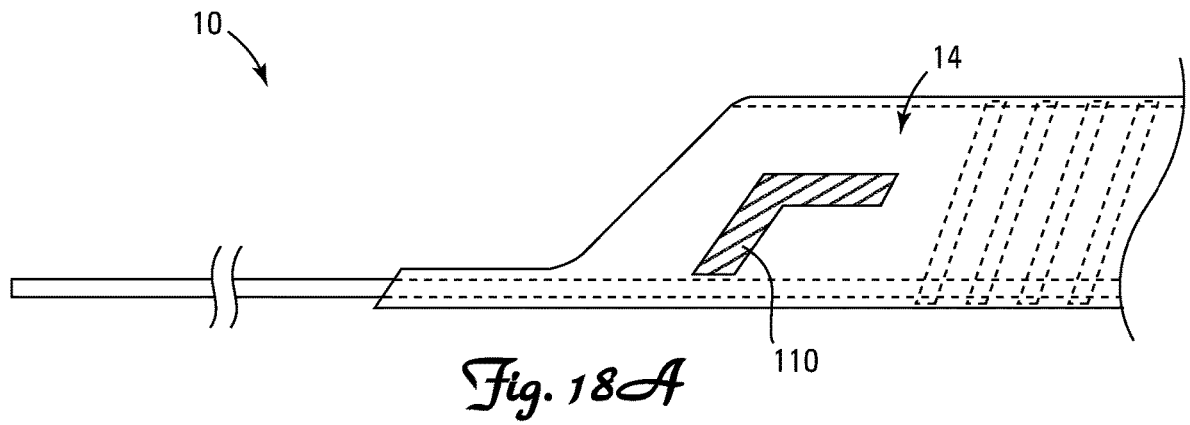
FIG. 18A is a cross-sectional side view of a boosting catheter showing the junction of the proximal and distal portions, according to one implementation.
Figure 18B:
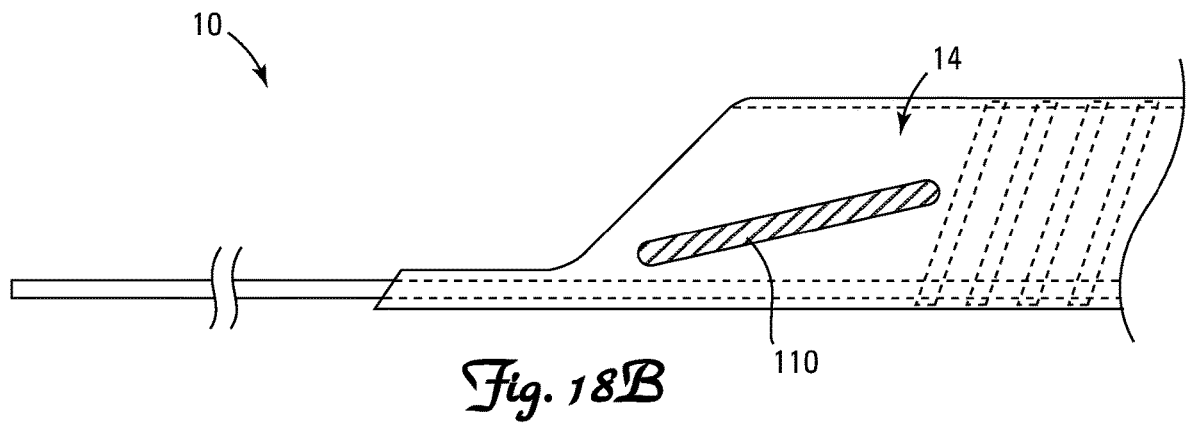
FIG. 18B is a cross-sectional side view of a boosting catheter showing the junction of the proximal and distal portions, according to another implementation.
Figure 18C:
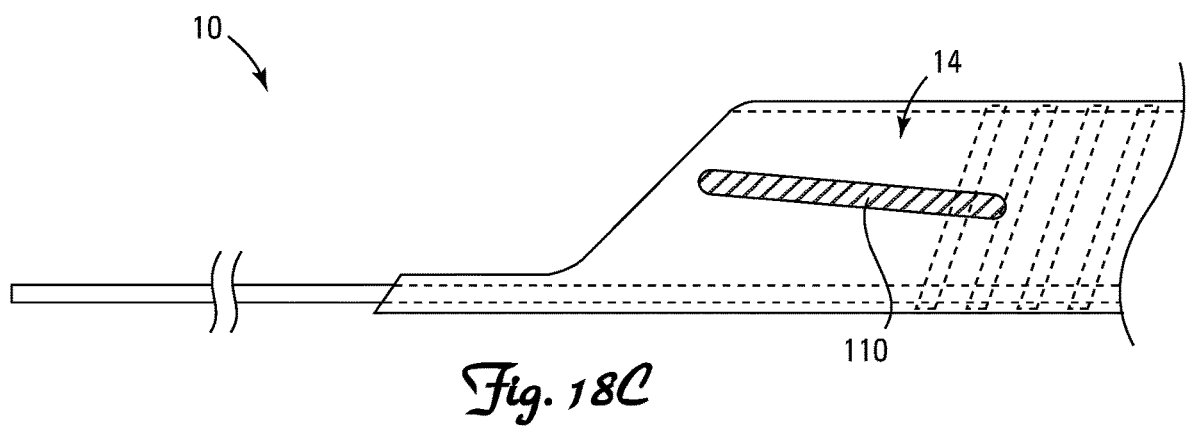
FIG. 18C is a cross-sectional side view of a boosting catheter showing the junction of the proximal and distal portions, according to a further implementation.

Other device 10 embodiments include additional support structure in the distal tube 14 that can provide mechanical advantage similar to that provided by the support coil. FIG. 18A depicts a device 10 having a distal tube 14 with a support member 110 positioned in the transition zone 40 that is configured to assume at least some of the mechanical loads. Alternatively, FIG. 18B depicts another embodiment of a support member 110 positioned in the transition zone 40 of a distal tube 14, while FIG. 18C shows a further implementation of a support member 110. In a further alternative, the tube 14 can have two or more support members. In certain embodiments, the support member (including the support members 110 depicted in FIGS. 18A-18C) can be the distal portion of the rod or tube extending distally from the shaft 16.

In use, the device 10 according to any of the embodiments disclosed herein can be used to conduct a predetermined amount of contrast solution (or any other fluid that could be used in this context as described above) from a reservoir in an operating room into a human body to a predetermined location. In one embodiment, the method can involve the steps of: introducing a guiding catheter into a human body along a predetermined pathway to a predetermined location; inserting the boosting catheter 10 into the guiding catheter, where the boosting catheter 10 includes the proximal portion 16 and the distal portion 14, and moving it distally along the guiding catheter a predetermined distance; introducing the solution into the proximal end of the proximal portion; conducting the fluid along the length of the proximal portion 16; and dispersing the solution distal of the proximal portion 16 into the human body in order to make the portion of the body (typically an artery or vein) visible to a doctor using an x-ray or similar device. It is further understood that any of the device implementations disclosed or contemplated herein can be used to perform any of the procedures described above with respect to FIG. 1.

Alternative manipulation shaft 16 embodiments are shown in FIGS. 19A-19D". These various shaft 16 embodiments have various opening configurations, including gradual tapered sections or tapered sections, including some such sections at the distal opening, at the distal end of the shaft 16. In certain implementations, the tapered section can be created via cutting or grinding processes. Alternatively, any known process for creating such a tapered configuration can be used.

Figure 19A:
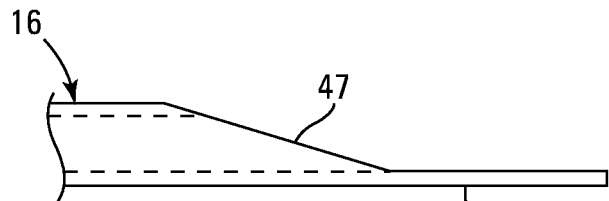
FIG. 19A is a cross-sectional side view of a proximal shaft of a boosting catheter, according to one embodiment.
Figure 19A:
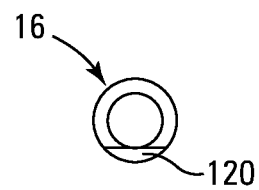
Figure 19B:
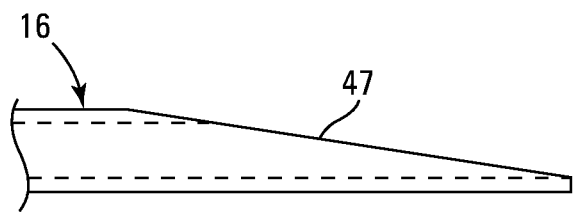
FIG. 19B is a cross-sectional side view of a proximal shaft of a boosting catheter, according to another embodiment.
Figure 19C:
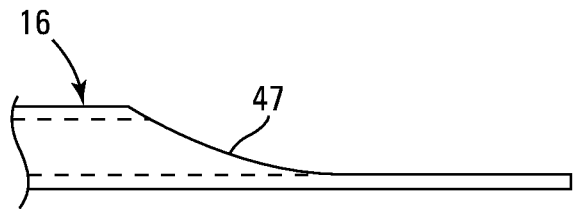
FIG. 19C is a cross-sectional side view of a proximal shaft of a boosting catheter, according to a further embodiment.
Figure 19D:
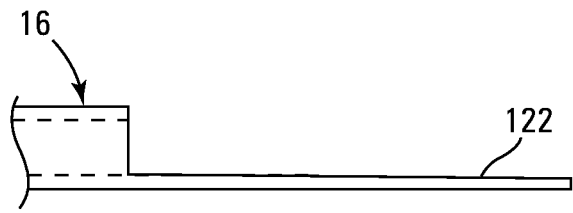
FIG. 19D is a cross-sectional side view of a proximal shaft of a boosting catheter, according to yet another embodiment.
Figure 19D:
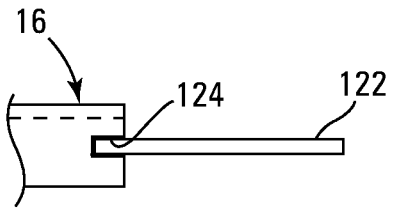
Figure 19D:
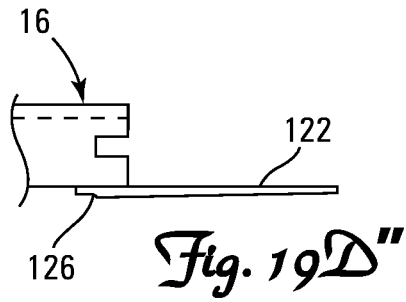

FIGS. 19A and 19A' show a shaft 16 having a shallow tapered section 47 and a straight extension 120. FIG. 19B depicts a shaft 16 having a tapered section 47 without a straight extension. FIG. 19C shows a shaft 16 with a curved tapered section 47. FIG. 19D shows a shaft 16 with a distal end that is perpendicular to the longitudinal axis of the shaft 16, and a short segment of flat wire 122 can be coupled to it, such as in a slot joint 124 (FIG. 6D') or a lap joint 126 (FIG. 6D"). These embodiments all define openings that are open to (i.e. in fluid communication with) the larger system. In other words, the openings permit fluid to flow out of the tube 16 and into blood that may be flowing around and past the openings.

Figure 20A:
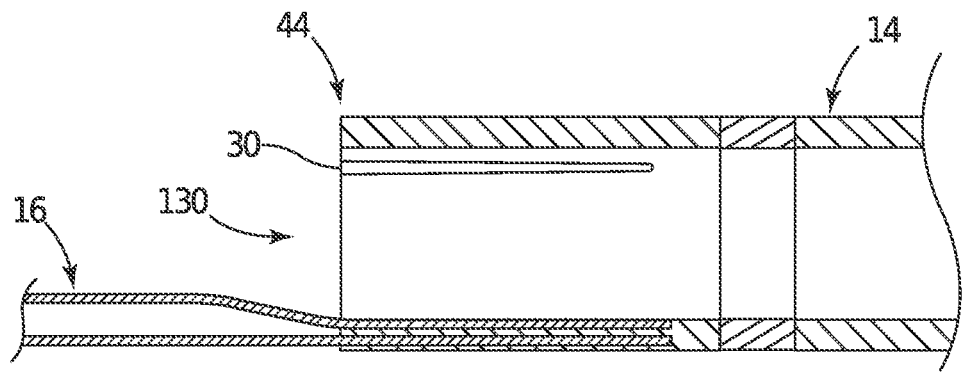
FIG. 20A is a cross-sectional side view of a boosting catheter showing the junction of the proximal and distal portions, according to one implementation.
Figure 20B:
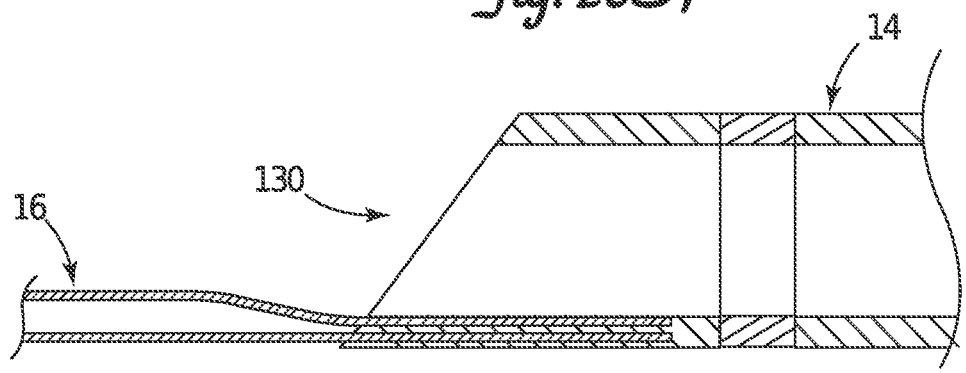
FIG. 20B is a cross-sectional side view of a boosting catheter showing the junction of the proximal and distal portions, according to another implementation.
Figure 20C:
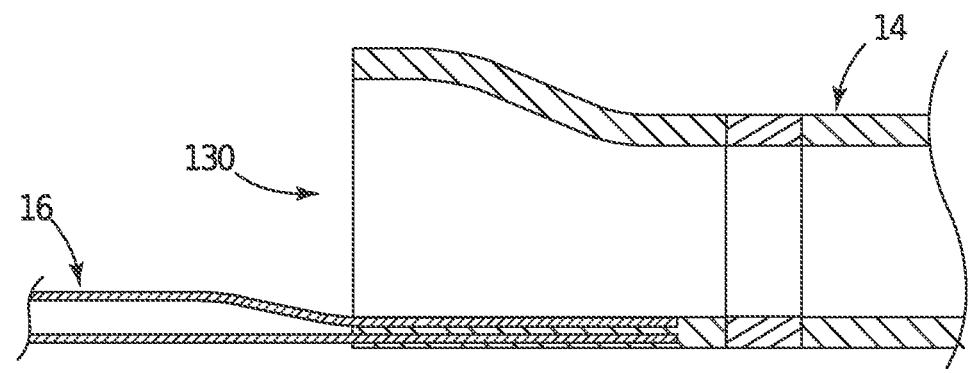
FIG. 20C is a cross-sectional side view of a boosting catheter showing the junction of the proximal and distal portions, according to a further implementation.

As shown in FIG. 20A, the proximal end 44 of the distal tube 14 may be configured so that the opening 130 is perpendicular to the axis of the tube 14. In other embodiments, the opening 130 can be tapered, as shown in FIG. 20B; or the opening 130 may be flared, as shown in FIG. 7C. Still further, the opening 130 may be extended with an axially-extending slit 30 in the wall of the tube, as shown in FIG. 20A. In these latter three embodiments, the purpose of the enlarged opening 130 (and the slit 30) is to facilitate movement of tools and medical devices along the axis of the boosting guide catheter.

Figure 20D:
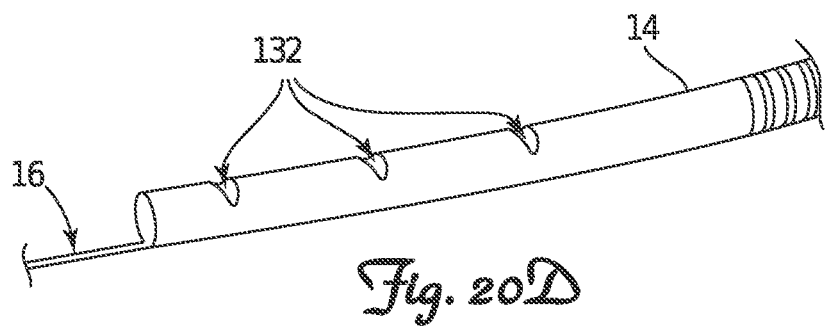
FIG. 20D is a perspective view of a boosting catheter showing the junction of the proximal and distal portions, according to another embodiment.

In a further implementation as shown in FIG. 20D, the proximal end of the distal tube 14 has one or more holes 132, slots, or any kind of openings defined in the wall of the tube 14. In the specific example depicted, the tube 14 has three slots 132, each of which has a long side that is perpendicular with the longitudinal axis of the tube 14. Alternatively, the tube 14 can have less than three or more than three holes. In accordance with certain embodiments, the one or more openings 132 can act as hinge-like components that allows for flexure of the proximal end of the tube 14 while minimizing or preventing buckling thereof.

Figure 21A:
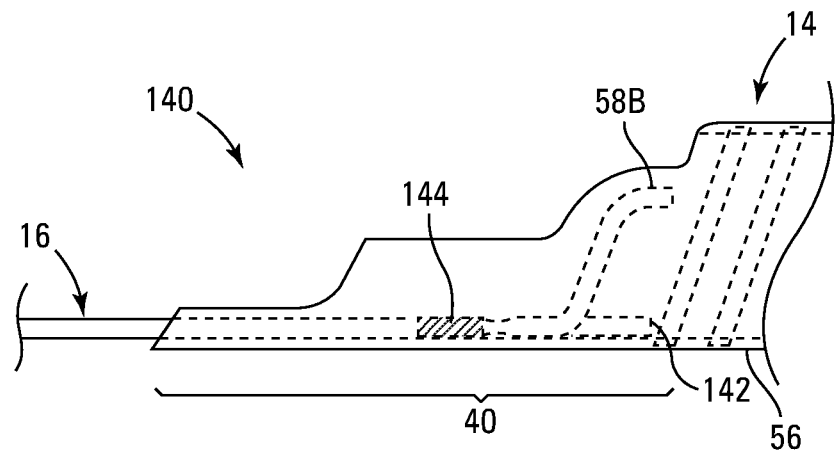
FIG. 21A is a cross-sectional side view of a boosting catheter showing the junction of the proximal and distal portions, according to one implementation.
Figure 21B:
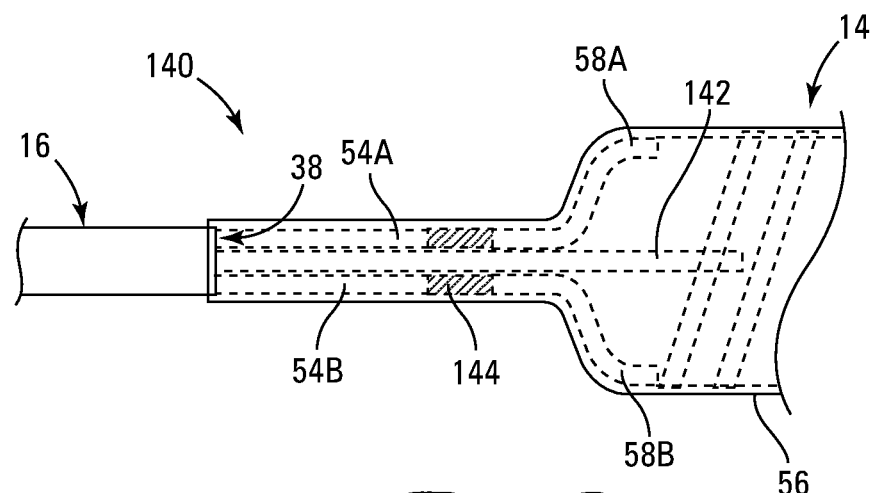
FIG. 21B is a cross-sectional top view of the boosting catheter of FIG. 21A.

According to a further embodiment depicted in FIGS. 21A and 21B, the device 140 has a manipulation shaft 16 that is made up of two rods 54A, 54B positioned within the lumen 38 of the shaft 16 (as best shown in FIG. 21B). FIG. 21A is a side view, while FIG. 21B is a top view. In this implementation, the shaft 16 is a polymeric coating 16 such as polyester and/or PET. A distal portion of the shaft 16 is coupled to and integral with an outer wall 56 of the distal tube 14 at the transition zone 40. Further, the two rods 54A, 54B extend from the distal portion of the shaft 16 such that the distal portions 58A, 58B of the rods 54A, 54B extend into the distal tube 14. More specifically, the distal portion 58A of rod 54A is disposed in the wall 56 of the distal tube 14 at a position that is on the opposite side of the wall 56 across the lumen 36 from the distal portion 58B. Further, as best shown in FIG. 21A, both distal portions 58A, 58B (only 58B is visible in FIG. 21A because of the location of distal portion 58A behind distal portion 58B in the figure) extend at an angle toward a vertical midpoint of the tube 14 and extend horizontally along that position for some distance as well as shown. In this specific implementation, both of the distal portions 58A, 58B of the rods 54A, 54B have a flat configuration, thereby reducing their profiles within the distal tube 14. In addition, in this implementation, a tube 142 is positioned between the two rods 54A, 54B, with the proximal end of the tube 142 extending into the shaft 16 and the distal end extending into the distal tube 14 as shown. It is understood that the proximal end of the tube 142 can be positioned at any point along the length of the manipulation shaft 16. Alternatively, the proximal end of the tube 142 can extend to the proximal end of the manipulation shaft 16. According to one embodiment, the tube 142 has a lumen (not shown) in fluid communication with the lumen 38 of the manipulation shaft 16 and further in fluid communication with the lumen 36 of the distal tube. Alternatively, the tube 142 can have a lumen (not shown) that is not in fluid communication with the lumen 38 or the lumen 36. In yet another alternative, the tube 142 has no lumen. Further, in this embodiment, two marker bands 144 are positioned around the rods 54A, 54B.

Figure 22A:
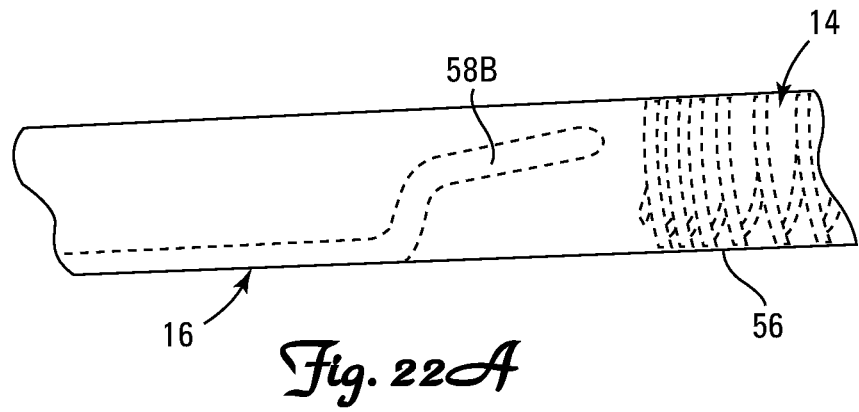
FIG. 22A is a perspective view of the side of a boosting catheter showing the junction of the proximal and distal portions, according to one implementation.
Figure 22B:
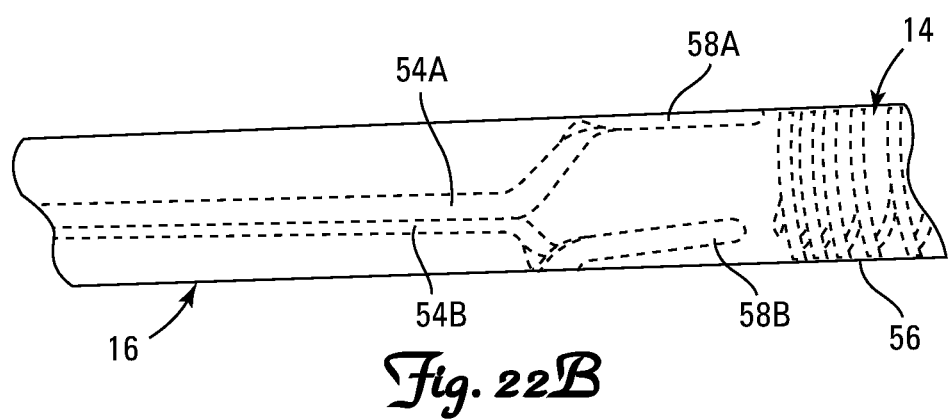
FIG. 22B is a perspective view of the top of the boosting catheter of FIG. 22A.
Figure 22C:
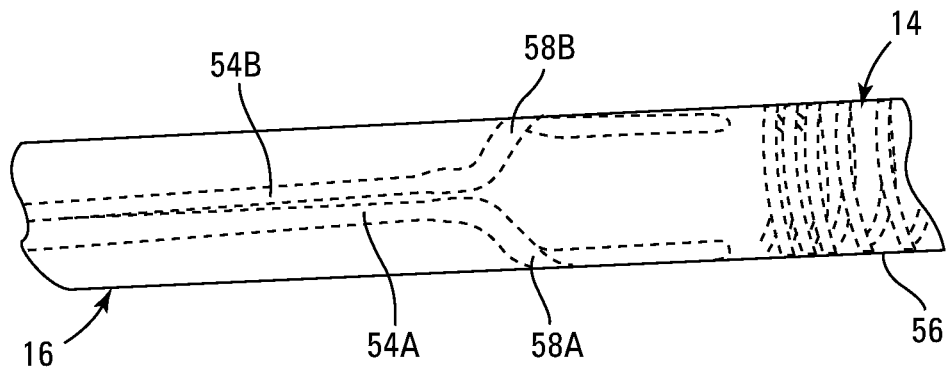
FIG. 22C is a perspective view of the underside of the boosting catheter of FIG. 22A.

FIGS. 22A, 22B, and 22C depict another device 150 having a manipulation shaft 16 that is made up of two rods 54A, 54B positioned within the lumen 38 of the shaft 16. FIG. 22A is a side view, while FIG. 22B is a top view and FIG. 22C is an underside view. As in the embodiment shown in FIGS. 21A and 21B, the two rods 54A, 54B extend into the distal tube 14. Further, the two distal portions 58A, 58B have a flat configuration as shown. The distal portion 58A is disposed in the wall 56 of the distal tube 14 at a position that is on the opposite side of the wall 56 across the lumen 36 from the distal portion 58B. Further, as best shown in FIG. 22A, both distal portions 58A, 58B (only 58B is visible in FIG. 22A because of the location of distal portion 58A behind distal portion 58B in the figure) extend at an angle toward a vertical midpoint of the tube 14 and extend horizontally along that position for some distance as well as shown. Unlike the prior embodiment (in FIGS. 21A and B), this implementation has no additional tube disposed between the two rods 58A, 58B.

What is claimed is:
1. A boosting catheter comprising:
 (a) a distal tube comprising:
  (i) a tubular wall;
  (ii) a tube lumen defined within the distal tube by the tubular wall;
  (iii) a proximal opening in fluidic communication with the tube lumen, wherein the proximal opening is sized to allow a medical device to be positioned through the proximal opening; and
  (iv) at least two openings defined within the tubular wall along a length of the distal tube, wherein the at least two openings are in fluidic communication with the tube lumen; and
 (b) a proximal shaft fixedly attached to a proximal portion of the distal tube, the proximal shaft comprising:
  (i) at least one shaft lumen defined in the proximal shaft; and
  (ii) at least one elongate member disposed within the at least one shaft lumen,
  wherein a distal end of the proximal shaft and a distal end of the at least one shaft lumen are disposed in the proximal portion of the distal tube,
  wherein the at least one shaft lumen is in fluidic communication with an area external to the catheter, and
  wherein an outer diameter of a length of the proximal shaft is less than a thickness of the tubular wall of the distal tube.

2. The boosting catheter of claim 1, further comprising a visual marker disposed on the distal tube or the proximal shaft.

3. The boosting catheter of claim 2, wherein the visual marker is a radiopaque marker.

4. The boosting catheter of claim 1, wherein the at least one elongate member defines a lumen within the at least one elongate member.

5. The boosting catheter of claim 1, wherein the proximal shaft is configured to extend into a portion of the distal tube such that the shaft lumen extends distally past a proximal end of the distal tube.

6. The boosting catheter of claim 1, wherein the at least two openings are defined within the tubular wall such that the tube lumen is in fluidic communication with the area external to the catheter.

7. The boosting catheter of claim 1, wherein the at least one elongate member comprises:
 (i) a first elongate member disposed within the at least one shaft lumen; and
 (ii) a second elongate member disposed within the at least one shaft lumen.

8. The boosting catheter of claim 1, wherein the at least one elongate member has no lumen.

9. The boosting catheter of claim 1, wherein the proximal shaft further comprises a tube disposed in the proximal shaft.

10. A boosting catheter comprising:
(a) a distal tube comprising:
(i) a tubular wall;
(ii) a tube lumen defined within the distal tube by the tubular wall;
(iii) a proximal opening in fluidic communication with the tube lumen, wherein the proximal opening is sized to allow a medical device to be positioned through the proximal opening; and
(iv) a plurality of openings defined within the tubular wall along a length of the distal tube, wherein the plurality of openings are in fluidic communication with the tube lumen such that the tube lumen is in fluidic communication with an area external to the catheter; and
(b) a proximal shaft operably coupled to a proximal portion of the distal tube, the proximal shaft comprising;
(i) a shaft lumen defined in the proximal shaft; and
(ii) at least one elongate member disposed within the shaft lumen,
wherein the proximal shaft is configured to extend into a portion of the tubular wall such that the shaft lumen extends distally past a proximal end of the distal tube and a distal end of the shaft lumen is disposed in the proximal portion of the distal tube, and
wherein the shaft lumen is in fluidic communication with the area external to the catheter.

11. The boosting catheter of claim 10, wherein the at least one elongate member comprises:
(i) a first elongate member disposed within the shaft lumen; and
(ii) a second elongate member disposed within the shaft lumen.

12. The boosting catheter of claim 11, wherein at least one of the first and second elongate members defines a lumen within the at least one of the first and second elongate members.

13. The boosting catheter of claim 11, wherein at least one of the first and second elongate members has no lumen.

14. The boosting catheter of claim 10, wherein the proximal shaft further comprises a tube disposed in the proximal shaft.

15. The boosting catheter of claim 10, further comprising a visual marker disposed on the distal tube or the proximal shaft.

* * * * *